United States Patent
Asakura et al.

(10) Patent No.: US 8,993,279 B2
(45) Date of Patent: *Mar. 31, 2015

(54) METHOD FOR PRODUCTION OF L-AMINO ACID

(75) Inventors: Yoko Asakura, Kawasaki (JP); Ippei Inoue, Kawasaki (JP); Hisashi Yasueda, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 837 days.

This patent is subject to a terminal disclaimer.

(21) Appl. No.: 12/533,061

(22) Filed: Jul. 31, 2009

(65) Prior Publication Data

US 2010/0028958 A1 Feb. 4, 2010

Related U.S. Application Data

(63) Continuation of application No. PCT/JP2008/051643, filed on Feb. 1, 2008.

(30) Foreign Application Priority Data

Feb. 1, 2007 (JP) ................................. 2007-022910

(51) Int. Cl.
*C12P 13/08* (2006.01)
*C12P 13/04* (2006.01)
*C12R 1/63* (2006.01)

(52) U.S. Cl.
CPC .................. *C12P 13/04* (2013.01); *C12P 13/08* (2013.01); *C12R 1/63* (2013.01)
USPC .............. 435/115; 435/6; 435/7.1; 435/320.1

(58) Field of Classification Search
None
See application file for complete search history.

(56) References Cited

U.S. PATENT DOCUMENTS

| | | | |
|---|---|---|---|
| 3,703,429 A | 11/1972 | Berger et al. | |
| 5,556,776 A * | 9/1996 | Tsuchiya et al. | 435/106 |
| 5,661,012 A | 8/1997 | Sano et al. | |
| 5,827,698 A | 10/1998 | Kikuchi et al. | |
| 5,830,716 A | 11/1998 | Kojima et al. | |
| 5,846,790 A * | 12/1998 | Kimura et al. | 435/110 |
| 5,932,453 A | 8/1999 | Kikuchi et al. | |
| 6,040,160 A | 3/2000 | Kojima et al. | |
| 6,436,630 B1 | 8/2002 | Remon et al. | |
| 6,878,533 B2 | 4/2005 | Tsujimoto et al. | |
| 6,911,332 B2 | 6/2005 | Usuda et al. | |
| 7,026,149 B2 | 4/2006 | Usuda et al. | |
| 7,029,893 B2 | 4/2006 | Usuda et al. | |
| 7,060,475 B2 | 6/2006 | Usuda et al. | |
| 7,160,704 B2 | 1/2007 | Takeshita et al. | |
| 7,169,587 B2 | 1/2007 | Gunji et al. | |
| 7,192,747 B2 | 3/2007 | Ono et al. | |
| 7,192,748 B2 | 3/2007 | Usuda et al. | |
| 7,211,416 B2 | 5/2007 | Asahara et al. | |
| 7,211,421 B2 | 5/2007 | Tsujimoto et al. | |
| 7,217,543 B2 | 5/2007 | Gunji et al. | |
| 7,220,570 B2 | 5/2007 | Usuda et al. | |
| 7,223,572 B1 | 5/2007 | Gunji et al. | |
| 7,261,899 B1 | 8/2007 | Carlin et al. | |
| 7,306,933 B2 | 12/2007 | Dien et al. | |
| 7,335,506 B2 | 2/2008 | Gunji et al. | |
| 7,381,548 B2 * | 6/2008 | Sheremet'eva et al. | 435/106 |
| 7,439,038 B2 | 10/2008 | Gunji et al. | |
| 7,833,761 B2 * | 11/2010 | Terashita et al. | 435/106 |
| 7,833,762 B2 * | 11/2010 | Kataoka et al. | 435/115 |
| 2002/0160461 A1 | 10/2002 | Nakai et al. | |
| 2005/0148048 A1 | 7/2005 | Hashimoto et al. | |
| 2006/0003424 A1 | 1/2006 | Asakura et al. | |
| 2006/0019355 A1 | 1/2006 | Ueda et al. | |
| 2006/0040365 A1 | 2/2006 | Kozlov et al. | |
| 2007/0249017 A1 | 10/2007 | Usuda et al. | |
| 2008/0038825 A1 | 2/2008 | Gunji et al. | |
| 2008/0199919 A1 | 8/2008 | Gunji et al. | |
| 2009/0104667 A1 | 4/2009 | Asakura et al. | |

FOREIGN PATENT DOCUMENTS

| | | |
|---|---|---|
| AU | 32883/68 | 8/1969 |
| EP | 0733710 | 9/1996 |
| EP | 0780477 | 6/1997 |
| EP | 1067193 | 1/2001 |
| EP | 1188822 | 3/2002 |
| JP | 49-12092 | 2/1974 |
| JP | 53-127892 | 11/1978 |
| JP | 56-85291 | 7/1981 |
| JP | 56-085291 | 7/1981 |
| JP | 60-062993 | 4/1985 |
| JP | 60-62993 | 4/1985 |
| JP | 62-239997 | 10/1987 |
| JP | 62-275696 | 11/1987 |
| JP | 62-289194 | 12/1987 |
| JP | 01-104190 | 4/1989 |
| JP | 2004-041035 | 2/2004 |
| JP | 2004-166640 | 6/2004 |
| WO | WO01/53459 | 7/2001 |
| WO | WO2005/042720 | 5/2005 |
| WO | WO2009/109102 | 9/2009 |

OTHER PUBLICATIONS

Lannotti et al. (J.Bacteriol. vol. 114, No. 3, 1973, pp. 1231-1240) Soda (Biotechnol. vol. 3, pp. 477-530).*
Panda et al. (Biotech & Bioengin., vol. 45, No. 3, 1995) Soda (Biochem. vol. 3, No. 10, 1964, pp. 1450-1451).*
Charlier et al. (Antonie van Leeuwenhoek, vol. 40, 1974, pp. 145-151) Ivins et al. (Infection & Immunity, 1980, vol. 27, No. 3, pp. 721-729).*
Soda et al, (Biochem. & Biophys. Res. Comm., vol. 44, No. 4, 1971).*

(Continued)

*Primary Examiner* — Hope Robinson
(74) *Attorney, Agent, or Firm* — Shelly Guest Cermak; Cermak Nakajima & McGowan LLP

(57) ABSTRACT

A method for producing an L-amino acid is described, which is characterized by culturing a *Vibrio* bacterium capable of producing the L-amino acid in a culture medium to produce and accumulate the L-amino acid in the culture medium and collecting the L-amino acid from the culture medium.

7 Claims, 3 Drawing Sheets

(56) References Cited

OTHER PUBLICATIONS

Muir et al (Nucleic Acid Research, vol. 18, No. 6, 1990, p. 1636).*
Munro et al. (Letters in Applied Microbio., 1994, vol. 18, pp. 197-199).*
Lakshmi et al. (Int'l J. of Advanced Biotech. & Research, vol. 2, Iss. 3, 2011, pp. 376-381).*
Berlin et al. (Applied & Environmental Micro., 1999, vol. 65 (6), pp. 2776-2780).*
Sawabe et al. (Int'l J. of Systematic & Evolutionary Microbiol., 2007, vol. 57, pp. 916-922).*
International Search Report for PCT Patent App. No. PCT/JP2008/051643 (Mar. 4, 2008).
Albright, L. J., et al., "Effects of Environmental Parameters of Low Temperature and Hydrostatic Pressure on L-Serine Deamination by *Vibrio marinus*," J. Oceanograph. Soc. Japan 1972;28(2):63-70.
Makino, K., et al., "Genome sequence of *Vibrio parahaemolytocus*: a pathogenic mechanism distinct from that of *V cholerae*," The Lancet 2003;361(9359):743-749.
Motoyama, H., et al., "Characterization of the Aspartate Family Amino Acids Biosynthetic Enzymes in L-Threonine- and L-Lysine-producing Mutants of *Methylobacillus glycogenes*," Biosci. Biotech. Biochem. 1993;57(3):461-466.
Supplementary European Search Report for EP Patent App. No. 08704352.7 (Mar. 26, 2010).
International Preliminary Report on Patentability for PCT Patent App. No. PCT/JP2008/051643 (Aug. 13, 2009).
Makino, K., et al., "Genome sequence of *Vibrio parahaemolyticus*: a pathogenic mechanism distinct from that of *V cholerae*," The Lancet 2003;361(9359):743-749.
Aspartokinase (Aspartate kinase), Protein database [online], National Center for Biontechnology Information, National Library of Medicine, Accession No. Q87LR4, created Jun. 1, 2003, accessed Feb. 15, 2008.
Aspartokinase 1/homoserine dehydrogenase, threonine-sensitive, Protein database [online], National Center for Biotechnology Information, National Library of Medicine, Accession No. Q87SD0, created Jun. 1, 2003, accessed Feb. 15, 2008.
Bifunctional aspartate kinase 2/homoserine dehydrogenase 2, Protein database [online], National Center for Biotechnology Information, National Library of Medicine, Accession No. Q1V6F6, created May 16, 2006, accessed Feb. 18, 2008.
Aspartokinase (Aspartate kinase), Protein database [online], National Center for Biotechnology Information, National Library of Medicine, Accesion No. Q87L96, created Jun. 1, 2003, accessed Feb. 18, 2008.
Putative aspartokinase, Protein database [online], National Center for Biotechnology Information, National Library of Medicine, Accession No. Q87NZ9, created Jun. 1, 2003, accessed Feb. 18, 2008.

* cited by examiner

SEQUENCE LISTING

```
<160> NUMBER OF SEQ ID NOS: 40

<210> SEQ ID NO 1
<211> LENGTH: 24
<212> TYPE: DNA
<213> ORGANISM: Artificial sequence
<220> FEATURE:
<223> OTHER INFORMATION: primer

<400> SEQUENCE: 1
cgtgcaaaag ttyggyggaa cytc                                          24

<210> SEQ ID NO 2
<211> LENGTH: 23
<212> TYPE: DNA
<213> ORGANISM: Artificial sequence
<220> FEATURE:
<223> OTHER INFORMATION: primer

<400> SEQUENCE: 2
caaatmttya cygaygtyga tgg                                           23

<210> SEQ ID NO 3
<211> LENGTH: 24
<212> TYPE: DNA
<213> ORGANISM: Artificial sequence
<220> FEATURE:
<223> OTHER INFORMATION: primer

<400> SEQUENCE: 3
acaagtrtaw atmccatcra crtc                                          24

<210> SEQ ID NO 4
<211> LENGTH: 25
<212> TYPE: DNA
<213> ORGANISM: Artificial sequence
<220> FEATURE:
<223> OTHER INFORMATION: primer

<400> SEQUENCE: 4
argymtcrtg maraatrttt gcygc                                         25

<210> SEQ ID NO 5
<211> LENGTH: 20
<212> TYPE: DNA
<213> ORGANISM: Artificial sequence
<220> FEATURE:
<223> OTHER INFORMATION: primer

<400> SEQUENCE: 5
```
ggaggaaggg atgcgagtat						20

<210> SEQ ID NO 6
<211> LENGTH: 22
<212> TYPE: DNA
<213> ORGANISM: Artificial sequence
<220> FEATURE:
<223> OTHER INFORMATION: primer

<400> SEQUENCE: 6
gcatcatcag taaaggtgar cg					22

<210> SEQ ID NO 7
<211> LENGTH: 23
<212> TYPE: DNA
<213> ORGANISM: Artificial sequence
<220> FEATURE:
<223> OTHER INFORMATION: primer

<400> SEQUENCE: 7
aacagcttya ayccwcaagg tgc					23

<210> SEQ ID NO 8
<211> LENGTH: 22
<212> TYPE: DNA
<213> ORGANISM: Artificial sequence
<220> FEATURE:
<223> OTHER INFORMATION: primer

<400> SEQUENCE: 8
tggtggatca ratycarcgt ca					22

<210> SEQ ID NO 9
<211> LENGTH: 22
<212> TYPE: DNA
<213> ORGANISM: Artificial sequence
<220> FEATURE:
<223> OTHER INFORMATION: primer

<400> SEQUENCE: 9
gcaccttgwg grttraagct gt					22

<210> SEQ ID NO 10
<211> LENGTH: 22
<212> TYPE: DNA
<213> ORGANISM: Artificial sequence
<220> FEATURE:
<223> OTHER INFORMATION: primer

<400> SEQUENCE: 10
tgacgytgra tytgatccac ca					22

<210> SEQ ID NO 11
<211> LENGTH: 23
<212> TYPE: DNA
<213> ORGANISM: Artificial sequence
<220> FEATURE:
<223> OTHER INFORMATION: primer

<400> SEQUENCE: 11
acrctracat taccaatkga agc					23

<210> SEQ ID NO 12
<211> LENGTH: 25
<212> TYPE: DNA
<213> ORGANISM: Artificial sequence
<220> FEATURE:
<223> OTHER INFORMATION: primer

<400> SEQUENCE: 12
ctgattgccg atctygayca agcct                                      25

<210> SEQ ID NO 13
<211> LENGTH: 23
<212> TYPE: DNA
<213> ORGANISM: Artificial sequence
<220> FEATURE:
<223> OTHER INFORMATION: primer

<400> SEQUENCE: 13
accatttgga gtgatgtkgc tgg                                        23

<210> SEQ ID NO 14
<211> LENGTH: 23
<212> TYPE: DNA
<213> ORGANISM: Artificial sequence
<220> FEATURE:
<223> OTHER INFORMATION: primer

<400> SEQUENCE: 14
ttrgtygcgg twgtcgatag cca                                        23

<210> SEQ ID NO 15
<211> LENGTH: 23
<212> TYPE: DNA
<213> ORGANISM: Artificial sequence
<220> FEATURE:
<223> OTHER INFORMATION: primer

<400> SEQUENCE: 15
takgtytggc tatcgacwac sgc                                        23

<210> SEQ ID NO 16
<211> LENGTH: 23
<212> TYPE: DNA
<213> ORGANISM: Artificial sequence
<220> FEATURE:
<223> OTHER INFORMATION: primer

<400> SEQUENCE: 16
ctytcratgg caaaratgtt gtc                                        23

<210> SEQ ID NO 17
<211> LENGTH: 23
<212> TYPE: DNA
<213> ORGANISM: Artificial sequence
<220> FEATURE:
<223> OTHER INFORMATION: primer

<400> SEQUENCE: 17
tgggagaawy gcmgtgagcr cat                                        23

<210> SEQ ID NO 18
<211> LENGTH: 26
<212> TYPE: DNA
<213> ORGANISM: Artificial sequence
<220> FEATURE:
<223> OTHER INFORMATION: primer

<400> SEQUENCE: 18
tcraasagct ctktatgcag cttctg                                     26

<210> SEQ ID NO 19
<211> LENGTH: 19
<212> TYPE: DNA
<213> ORGANISM: Artificial sequence
<220> FEATURE:
<223> OTHER INFORMATION: primer

<400> SEQUENCE: 19
tcatgacttw taccgtaga                                                   19

<210> SEQ ID NO 20
<211> LENGTH: 20
<212> TYPE: DNA
<213> ORGANISM: Artificial sequence
<220> FEATURE:
<223> OTHER INFORMATION: primer

<400> SEQUENCE: 20
gtaatcgagt trgcgttcat                                                  20

<210> SEQ ID NO 21
<211> LENGTH: 1779
<212> TYPE: DNA
<213> ORGANISM: Vibrio natriegens
<220> FEATURE:
<221> NAME/KEY: CDS
<222> LOCATION: (526)..(1710)

<400> SEQUENCE: 21
agtacgcgtt atacgactca ctatagggag atctagaagg tgctgacagc aaaaacctac      60
gtactatggt tgatgatatc aagaaccaaa tgggttctgg tgttgtactt ctggctaaca     120
tcacgggtga caaagttggt ttgatcgctg gtgtaactaa agatctggtt ggcaaagtca     180
aagcgggtga tttagttaaa atggtagcag agcaggttgg tggtaaaggc ggcggtcgtc     240
ctgatatggc gcaagctggc ggtactgacg tagcggcact tccagaagca atcaaaactg     300
ttcagccttg gctagaagag cgcttgtaac aagctataaa taacaaatat acgctcaatc     360
aatttgtttt gattgggcgt aatttttta agttgaccaa gtggtttaat ggaccagaga     420
ttaagctggc ccactaagct gcttggtttt tcttgtaact accacttata taaacagaat     480
gtatgtggtc cgaatgagac tttggtcttg gaaggtgaa gactg gtg aaa aag ccc     537
                                                 Val Lys Lys Pro
                                                  1 ctt atc gtg caa aag ttt ggc gga acc tct gtg ggt tca att gaa aga      585
Leu Ile Val Gln Lys Phe Gly Gly Thr Ser Val Gly Ser Ile Glu Arg
 5                  10                  15                  20 atc cac caa gtt gct gaa cac atc att aag gcg aaa aat gat ggt aat      633
Ile His Gln Val Ala Glu His Ile Ile Lys Ala Lys Asn Asp Gly Asn
                 25                  30                  35 caa gtt gtt gta gtt gtg tct gct atg tca ggc gaa acc aat agg ctt      681
Gln Val Val Val Val Val Ser Ala Met Ser Gly Glu Thr Asn Arg Leu
             40                  45                  50 atg gac cta gct aaa cag gta gat agc gtt cct aca gcc cga gaa ctt      729
Met Asp Leu Ala Lys Gln Val Asp Ser Val Pro Thr Ala Arg Glu Leu
         55                  60                  65 gat gtt ttg ctc tct gct ggt gag caa gtg tcg atg gca ctg ttg gcg      777
Asp Val Leu Leu Ser Ala Gly Glu Gln Val Ser Met Ala Leu Leu Ala
     70                  75                  80 atg aca ctg aac aaa atg ggt cat cct gca cgc tca ctt acc gga gca      825
Met Thr Leu Asn Lys Met Gly His Pro Ala Arg Ser Leu Thr Gly Ala
 85                  90                  95                 100

| | | |
|---|---|---|
| cag gcg aac att gtg act gat aac cag cac aat gac gca acg att aag<br>Gln Ala Asn Ile Val Thr Asp Asn Gln His Asn Asp Ala Thr Ile Lys<br>105 110 115 | | 873 |
| cac att gat act acg aga gtg atg gca ttg ctt gaa caa gag cat gtc<br>His Ile Asp Thr Thr Arg Val Met Ala Leu Leu Glu Gln Glu His Val<br>120 125 130 | | 921 |
| gtt atc gtc gca ggt ttt cag ggt gtg aat gaa aat ggg gat atc acc<br>Val Ile Val Ala Gly Phe Gln Gly Val Asn Glu Asn Gly Asp Ile Thr<br>135 140 145 | | 969 |
| aca tta ggt cga gga ggc tca gat acg agc gca gtg aca ctg gct ggt<br>Thr Leu Gly Arg Gly Gly Ser Asp Thr Ser Ala Val Thr Leu Ala Gly<br>150 155 160 | | 1017 |
| gca cta cgt gct gat gag tgt caa atc ttt acc gac gtt gat ggt att<br>Ala Leu Arg Ala Asp Glu Cys Gln Ile Phe Thr Asp Val Asp Gly Ile<br>165 170 175 180 | | 1065 |
| tat act tgt gac cca cgt gta gta aaa acg gcg caa aaa atg gca gtg<br>Tyr Thr Cys Asp Pro Arg Val Val Lys Thr Ala Gln Lys Met Ala Val<br>185 190 195 | | 1113 |
| att gac ttt cct tca atg gaa gca atg gca agc cgt ggt gct aaa gtt<br>Ile Asp Phe Pro Ser Met Glu Ala Met Ala Ser Arg Gly Ala Lys Val<br>200 205 210 | | 1161 |
| tta cat tta cct tcg gtg caa tat gca tgg aag aac aat gta cca cta<br>Leu His Leu Pro Ser Val Gln Tyr Ala Trp Lys Asn Asn Val Pro Leu<br>215 220 225 | | 1209 |
| cgc gtg ctt tct aca ttc gat gtg aat gaa ggt agt tta gtt aag gga<br>Arg Val Leu Ser Thr Phe Asp Val Asn Glu Gly Ser Leu Val Lys Gly<br>230 235 240 | | 1257 |
| gag att ggc aca caa gcc atc tct ggt ata gct att caa cga gac ctt<br>Glu Ile Gly Thr Gln Ala Ile Ser Gly Ile Ala Ile Gln Arg Asp Leu<br>245 250 255 260 | | 1305 |
| gcc att att gaa gta gat aaa gaa cat ttg tcc agt gct aca aag caa<br>Ala Ile Ile Glu Val Asp Lys Glu His Leu Ser Ser Ala Thr Lys Gln<br>265 270 275 | | 1353 |
| tgt cag atg cta ggt atc gat gtc tgg aat gtg atc gag gaa aca gaa<br>Cys Gln Met Leu Gly Ile Asp Val Trp Asn Val Ile Glu Glu Thr Glu<br>280 285 290 | | 1401 |
| cgg aca ggt atc atg ata aaa caa gat gca tgt gcc aag ttc gat ctg<br>Arg Thr Gly Ile Met Ile Lys Gln Asp Ala Cys Ala Lys Phe Asp Leu<br>295 300 305 | | 1449 |
| gtg ttc agc gat aaa atc cgt aat agt gaa atg gta agc ctg ttg acc<br>Val Phe Ser Asp Lys Ile Arg Asn Ser Glu Met Val Ser Leu Leu Thr<br>310 315 320 | | 1497 |
| gca gta ggg ctt gag gcc aat gga atg gtc gag cat gca tgc gat ttg<br>Ala Val Gly Leu Glu Ala Asn Gly Met Val Glu His Ala Cys Asp Leu<br>325 330 335 340 | | 1545 |
| ctg gct gag caa gat att gcg atc aat ttc tgc gca acg aat gca ctc<br>Leu Ala Glu Gln Asp Ile Ala Ile Asn Phe Cys Ala Thr Asn Ala Leu<br>345 350 355 | | 1593 |
| act atg atg cta gta tta tct cct gac tgt gtg gat atg gcg gca aac<br>Thr Met Met Leu Val Leu Ser Pro Asp Cys Val Asp Met Ala Ala Asn<br>360 365 370 | | 1641 |
| att ctt cat gat gct tac att acg tct agt gaa gcg tta agc att cag<br>Ile Leu His Asp Ala Tyr Ile Thr Ser Ser Glu Ala Leu Ser Ile Gln<br>375 380 385 | | 1689 |
| caa aaa cat gcc cta ata ggg tgatttcgct aacaaggtag tttacgaaaa<br>Gln Lys His Ala Leu Ile Gly<br>390 395 | | 1740 |
| tataactttt gttggataat agcgtgatag caagaaaat | | 1779 |

```
<210> SEQ ID NO 22
<211> LENGTH: 395
<212> TYPE: PRT
<213> ORGANISM: Vibrio natriegens

<400> SEQUENCE: 22

Val Lys Lys Pro Leu Ile Val Gln Lys Phe Gly Gly Thr Ser Val Gly
  1               5                  10                  15

Ser Ile Glu Arg Ile His Gln Val Ala Glu His Ile Ile Lys Ala Lys
             20                  25                  30

Asn Asp Gly Asn Gln Val Val Val Ser Ala Met Ser Gly Glu
         35                  40                  45

Thr Asn Arg Leu Met Asp Leu Ala Lys Gln Val Asp Ser Val Pro Thr
     50                  55                  60

Ala Arg Glu Leu Asp Val Leu Ser Ala Gly Glu Gln Val Ser Met
 65                  70                  75                  80

Ala Leu Leu Ala Met Thr Leu Asn Lys Met Gly His Pro Ala Arg Ser
                 85                  90                  95

Leu Thr Gly Ala Gln Ala Asn Ile Val Thr Asp Asn Gln His Asn Asp
            100                 105                 110

Ala Thr Ile Lys His Ile Asp Thr Thr Arg Val Met Ala Leu Leu Glu
        115                 120                 125

Gln Glu His Val Val Ile Val Ala Gly Phe Gln Gly Val Asn Glu Asn
    130                 135                 140

Gly Asp Ile Thr Thr Leu Gly Arg Gly Gly Ser Asp Thr Ser Ala Val
145                 150                 155                 160

Thr Leu Ala Gly Ala Leu Arg Ala Asp Glu Cys Gln Ile Phe Thr Asp
                165                 170                 175

Val Asp Gly Ile Tyr Thr Cys Asp Pro Arg Val Val Lys Thr Ala Gln
            180                 185                 190

Lys Met Ala Val Ile Asp Phe Pro Ser Met Glu Ala Met Ala Ser Arg
        195                 200                 205

Gly Ala Lys Val Leu His Leu Pro Ser Val Gln Tyr Ala Trp Lys Asn
    210                 215                 220

Asn Val Pro Leu Arg Val Leu Ser Thr Phe Asp Val Asn Glu Gly Ser
225                 230                 235                 240

Leu Val Lys Gly Glu Ile Gly Thr Gln Ala Ile Ser Gly Ile Ala Ile
                245                 250                 255

Gln Arg Asp Leu Ala Ile Ile Glu Val Asp Lys Glu His Leu Ser Ser
            260                 265                 270

Ala Thr Lys Gln Cys Gln Met Leu Gly Ile Asp Val Trp Asn Val Ile
        275                 280                 285

Glu Glu Thr Glu Arg Thr Gly Ile Met Ile Lys Gln Asp Ala Cys Ala
    290                 295                 300

Lys Phe Asp Leu Val Phe Ser Asp Lys Ile Arg Asn Ser Glu Met Val
305                 310                 315                 320

Ser Leu Leu Thr Ala Val Gly Leu Glu Ala Asn Gly Met Val Glu His
                325                 330                 335

Ala Cys Asp Leu Leu Ala Glu Gln Asp Ile Ala Ile Asn Phe Cys Ala
            340                 345                 350

Thr Asn Ala Leu Thr Met Met Leu Val Leu Ser Pro Asp Cys Val Asp
        355                 360                 365

Met Ala Ala Asn Ile Leu His Asp Ala Tyr Ile Thr Ser Ser Glu Ala
    370                 375                 380
```

```
Leu Ser Ile Gln Gln Lys His Ala Leu Ile Gly
385             390                 395

<210> SEQ ID NO 23
<211> LENGTH: 3547
<212> TYPE: DNA
<213> ORGANISM: Vibrio natriegens
<220> FEATURE:
<221> NAME/KEY: CDS
<222> LOCATION: (486)..(2942)

<400> SEQUENCE: 23
ttaaattgtt gtgcaagagt ggttgctctg cattttcttt gatctttgcc gttttagcca      60
agatcgccat gaatgtgggt ggaatgtaac tttttctatg caaagctatt tcgggaatga     120
aatactaaga taaatttatt aaaaaaattg aatttaatt tatttctttg ttttcagtga      180
tatatagcag aatttatctc tgcaagactg gaaataaac aattttttg ttgactctgt      240 tacagaaact cggtaaacgt agggttaagc aaacacacaa ttcgtagaat attaatttat     300
gccagttaac agcctcgttg taatgaccac caccattatt attaccgaca ttacaattgt     360
aggggcaggc tgctgagcga agaaattca caaaaaaggc ctgtatccaa caagatacag     420
gccttttttt atgctttctt aatacaaaat ttagacaagt ttagaagat acactggagg     480 aaggg atg cga gta ttg aag ttt ggc ggt tca tca ttg gct gat gca gat     530
      Met Arg Val Leu Lys Phe Gly Gly Ser Ser Leu Ala Asp Ala Asp
        1               5                  10                  15 cgc ttt tta aga gca gca gat atc att gcg aat aat gct caa cag gaa      578
Arg Phe Leu Arg Ala Ala Asp Ile Ile Ala Asn Asn Ala Gln Gln Glu
             20                  25                  30 gaa gtc gca gtc gtg ctt tct gca ccg ggt aaa aca act aat aaa ctg      626
Glu Val Ala Val Val Leu Ser Ala Pro Gly Lys Thr Thr Asn Lys Leu
         35                  40                  45 gtt gct gtg att gaa ggc gct ttg cga aat ggt gaa gca gaa tta caa      674
Val Ala Val Ile Glu Gly Ala Leu Arg Asn Gly Glu Ala Glu Leu Gln
     50                  55                  60 att aac gag tta gaa gaa tcg ttt aaa acg ctt ttt gcc gat atc caa      722
Ile Asn Glu Leu Glu Glu Ser Phe Lys Thr Leu Phe Ala Asp Ile Gln
 65                  70                  75 gcc ttg gtt cct aat ctg gat ggg act ggc tac gac aat caa gtt aaa      770
Ala Leu Val Pro Asn Leu Asp Gly Thr Gly Tyr Asp Asn Gln Val Lys
 80                  85                  90                  95 acc tcg ctc tct caa tta cgt caa ttt gtc cat ggc atc agc ctg tta      818
Thr Ser Leu Ser Gln Leu Arg Gln Phe Val His Gly Ile Ser Leu Leu
                100                 105                 110 ggc atg tgt cca aac aat gtg aat gcg cgc atc atc agt aaa ggt gaa      866
Gly Met Cys Pro Asn Asn Val Asn Ala Arg Ile Ile Ser Lys Gly Glu
            115                 120                 125 cgt gtt tct att caa cta atg aaa gcg gta ctt gaa gca aaa ggt caa      914
Arg Val Ser Ile Gln Leu Met Lys Ala Val Leu Glu Ala Lys Gly Gln
        130                 135                 140 aaa gcc agc cta att gat ccg gtt gaa tac ctt tat gct caa ggc gat      962
Lys Ala Ser Leu Ile Asp Pro Val Glu Tyr Leu Tyr Ala Gln Gly Asp
    145                 150                 155 cat ctt gaa gcg atg gtt gat gtt gat att tct aca caa aac ttc cgc     1010
His Leu Glu Ala Met Val Asp Val Asp Ile Ser Thr Gln Asn Phe Arg
160                 165                 170                 175 caa aag cct ctt cct caa ggt cat gtc aac atc atg cct ggt ttt act     1058
Gln Lys Pro Leu Pro Gln Gly His Val Asn Ile Met Pro Gly Phe Thr
                180                 185                 190 gcc ggc aat gag aaa gga gaa ctg gtt act cta ggt cgt aac ggt tca     1106
```

|     |     |     |     |     |     |     |     |     |     |     |     |      |
|-----|-----|-----|-----|-----|-----|-----|-----|-----|-----|-----|-----|------|
| Ala | Gly | Asn | Glu | Lys | Gly | Glu | Leu | Val | Thr | Leu | Gly | Arg Asn Gly Ser |
|     |     |     | 195 |     |     |     | 200 |     |     |     | 205 |      |

```
gac tat tcg gct gcg gtt ttg gct gct tgt ctt cgc gcc gat tgt tgt       1154
Asp Tyr Ser Ala Ala Val Leu Ala Ala Cys Leu Arg Ala Asp Cys Cys
            210                 215                 220 gaa atc tgg act gac gtt gat ggc gta tac aac tgt gat cct cgc ttg       1202
Glu Ile Trp Thr Asp Val Asp Gly Val Tyr Asn Cys Asp Pro Arg Leu
    225                 230                 235 gta gaa gat gca cga cta tta aaa tca ctg agc tat cag gaa gcg atg       1250
Val Glu Asp Ala Arg Leu Leu Lys Ser Leu Ser Tyr Gln Glu Ala Met
240                 245                 250                 255 gag ttg tct tac ttc ggt gcg tcc gtt ctg cac ccg aaa acc atc gct       1298
Glu Leu Ser Tyr Phe Gly Ala Ser Val Leu His Pro Lys Thr Ile Ala
                260                 265                 270 cca att gct caa ttc cac att cca tgc tta atc aag aac agt ttt aac       1346
Pro Ile Ala Gln Phe His Ile Pro Cys Leu Ile Lys Asn Ser Phe Asn
            275                 280                 285 ccg caa ggt gca ggt acg ctg att ggc caa gat act ggt gaa gat aac       1394
Pro Gln Gly Ala Gly Thr Leu Ile Gly Gln Asp Thr Gly Glu Asp Asn
        290                 295                 300 ctg gct atc aag ggt att act act ctg aat gac ctg acc atg gtg aac       1442
Leu Ala Ile Lys Gly Ile Thr Thr Leu Asn Asp Leu Thr Met Val Asn
305                 310                 315 gtt tct ggg cca ggt atg aaa ggc atg gtt ggc atg gcg agc cgt gta       1490
Val Ser Gly Pro Gly Met Lys Gly Met Val Gly Met Ala Ser Arg Val
320                 325                 330                 335 ttt ggt gct atg tct tca gcg ggt gtt tca atc gta ctg atc act cag       1538
Phe Gly Ala Met Ser Ser Ala Gly Val Ser Ile Val Leu Ile Thr Gln
                340                 345                 350 tca tca tca gaa tac agc atc agc ttc tgt atc gaa gca gaa gat aaa       1586
Ser Ser Ser Glu Tyr Ser Ile Ser Phe Cys Ile Glu Ala Glu Asp Lys
            355                 360                 365 gca aaa gcg cag cag aca ctg gca gaa gcg ttt gag ctt gaa ctg aaa       1634
Ala Lys Ala Gln Gln Thr Leu Ala Glu Ala Phe Glu Leu Glu Leu Lys
        370                 375                 380 gat ggt ctg ctt gaa cca gta gag ttt atc gat gat gtt gct atc gtg       1682
Asp Gly Leu Leu Glu Pro Val Glu Phe Ile Asp Asp Val Ala Ile Val
385                 390                 395 acc ctt gtt ggt gac ggc atg cgt aca tca cgt ggt gtg gct tca cgt       1730
Thr Leu Val Gly Asp Gly Met Arg Thr Ser Arg Gly Val Ala Ser Arg
400                 405                 410                 415 ttc ttc tca tct ctt gct gaa gta aac gtc aac att gtt gca atc gca       1778
Phe Phe Ser Ser Leu Ala Glu Val Asn Val Asn Ile Val Ala Ile Ala
                420                 425                 430 cag ggt tct tca gag cgc gct atc tca gcg gta atc cca gaa gat aag       1826
Gln Gly Ser Ser Glu Arg Ala Ile Ser Ala Val Ile Pro Glu Asp Lys
            435                 440                 445 atc tct gaa gca atc aaa gcc tgt cac atg aac ctg ttc aat tct aaa       1874
Ile Ser Glu Ala Ile Lys Ala Cys His Met Asn Leu Phe Asn Ser Lys
        450                 455                 460 cac ttc ctt gat gtt ttc gtc gta ggc atc ggc ggt gtt ggt ggc gag       1922
His Phe Leu Asp Val Phe Val Val Gly Ile Gly Gly Val Gly Gly Glu
465                 470                 475 ctg gtg gat cag att gaa cgc caa caa gct aaa ctg gca gaa aaa ggc       1970
Leu Val Asp Gln Ile Glu Arg Gln Gln Ala Lys Leu Ala Glu Lys Gly
480                 485                 490                 495 atc atc att cgc gta tgt ggt ctg gca aac agt aag ggt ctg ctt ctg       2018
Ile Ile Ile Arg Val Cys Gly Leu Ala Asn Ser Lys Gly Leu Leu Leu
                500                 505                 510
```

```
                                                    -continued gat agt gaa ggg ctg cca ctg gaa cac tgg cgc gac cgc atg tct tca    2066
Asp Ser Glu Gly Leu Pro Leu Glu His Trp Arg Asp Arg Met Ser Ser
        515                 520                 525 gcc act gaa gag ttc agc cta gcg cgc ctg att gca ctt gtg caa cgt    2114
Ala Thr Glu Glu Phe Ser Leu Ala Arg Leu Ile Ala Leu Val Gln Arg
        530                 535                 540 aac cac atc att aac cct gtt ttg gtt gat tgt act tcg agt gaa gcc    2162
Asn His Ile Ile Asn Pro Val Leu Val Asp Cys Thr Ser Ser Glu Ala
        545                 550                 555 att gct aac cag tac gct gat ttc ttg gcg gca ggt ttc cac gtt gtt    2210
Ile Ala Asn Gln Tyr Ala Asp Phe Leu Ala Ala Gly Phe His Val Val
560                 565                 570                 575 act cca aat aag aaa gcc aat aca gca agc atg gct tac tac cac cag    2258
Thr Pro Asn Lys Lys Ala Asn Thr Ala Ser Met Ala Tyr Tyr His Gln
        580                 585                 590 ctt cgc gat gta gca cgc agc tct cgt cgt aaa ttg atg tac gag aca    2306
Leu Arg Asp Val Ala Arg Ser Ser Arg Arg Lys Leu Met Tyr Glu Thr
        595                 600                 605 acg gtt ggt gcg ggt ttg ccg gtt atc gaa aac ctg cag aat ctc att    2354
Thr Val Gly Ala Gly Leu Pro Val Ile Glu Asn Leu Gln Asn Leu Ile
        610                 615                 620 tca gcg ggt gat gag ctt gaa cga ttc acc ggc att ttg tct ggt tca    2402
Ser Ala Gly Asp Glu Leu Glu Arg Phe Thr Gly Ile Leu Ser Gly Ser
625                 630                 635 cta tct tac atc ttc ggt aag cta gac gaa ggc atg agc ttg agc gaa    2450
Leu Ser Tyr Ile Phe Gly Lys Leu Asp Glu Gly Met Ser Leu Ser Glu
640                 645                 650                 655 gcg acc aac atc gcg aaa gaa aac ggc ttc acc gaa ccg gat cct cgt    2498
Ala Thr Asn Ile Ala Lys Glu Asn Gly Phe Thr Glu Pro Asp Pro Arg
        660                 665                 670 gat gat cta tcg ggt atg gat gtg gct cgt aag ctt ctt att ctg gcg    2546
Asp Asp Leu Ser Gly Met Asp Val Ala Arg Lys Leu Leu Ile Leu Ala
        675                 680                 685 cgt gaa gcg gga atg tcg cta gag ttg gaa gac gtt gtg gtt gat caa    2594
Arg Glu Ala Gly Met Ser Leu Glu Leu Glu Asp Val Val Val Asp Gln
        690                 695                 700 gcg ctg cca ccg ggc ttt gat gat tca ggc agt gtt gat gag ttt atg    2642
Ala Leu Pro Pro Gly Phe Asp Asp Ser Gly Ser Val Asp Glu Phe Met
705                 710                 715 gcg aga ctt cct gaa gct gat gcg tac ttt aaa gat ctt gtc gca aaa    2690
Ala Arg Leu Pro Glu Ala Asp Ala Tyr Phe Lys Asp Leu Val Ala Lys
720                 725                 730                 735 gcc gct gaa gag ggt aaa gtt tta cgt tat gtt ggt gaa atc aat gat    2738
Ala Ala Glu Glu Gly Lys Val Leu Arg Tyr Val Gly Glu Ile Asn Asp
        740                 745                 750 ggt aag tgc aaa gtc agc att gct atc gtt gat gaa aat gat cca atg    2786
Gly Lys Cys Lys Val Ser Ile Ala Ile Val Asp Glu Asn Asp Pro Met
        755                 760                 765 ttc aaa att aaa gat ggt gag aac gct ctg gcg ttt tac agc cgt tac    2834
Phe Lys Ile Lys Asp Gly Glu Asn Ala Leu Ala Phe Tyr Ser Arg Tyr
        770                 775                 780 tac caa cca atc cca ttg gta ctt cgt ggt tac ggt gca ggt acg gaa    2882
Tyr Gln Pro Ile Pro Leu Val Leu Arg Gly Tyr Gly Ala Gly Thr Glu
785                 790                 795 gtt acc gca gca ggc gta ttt tca gat gtg atg cgt act tta ggt tgg    2930
Val Thr Ala Ala Gly Val Phe Ser Asp Val Met Arg Thr Leu Gly Trp
800                 805                 810                 815 aaa cta ggg gta taacagtaat gagttcaagt gatatggatg tagtggttta         2982
Lys Leu Gly Val
```

```
tgccccagca tcaattggta atgtaagcgt aggttttgat gttttgggag cggctgtctc    3042
tcctatcgat ggcaccttat tgggtgatcg agtcctagtg aaatctggtt ctgagccatt    3102
tagcttgaaa accgcaggta acttcgtctc gaagttacct acagaaccaa agaaaaacat    3162
cgtttacgac tgttgggttg tatttgctcg gagctagat agaaagggcg cagagctgaa    3222
accattggaa atgacactcg agaagaacat gcctatcggt tctggtcttg gttccagtgc    3282
ttgttctatt gttgctgcat tagatgcttt gaaccgtttt cacgggcaac cacttaatga    3342
aactgagctg ttagcgctaa tgggcgagat ggaaggtaaa atttctggtg gtatccatta    3402
tgacaacgtt gcaccttgtt acttaggtgg cgtgcagttg atgcttgaag agcttggtat    3462
cattagccag gaagtgccat gttttgatga ctggtactgg gtaatggctt atccgggaat    3522
caaagtgtct actgctgaag ctcga                                          3547
```

<210> SEQ ID NO 24
<211> LENGTH: 819
<212> TYPE: PRT
<213> ORGANISM: Vibrio natriegens

<400> SEQUENCE: 24

```
Met Arg Val Leu Lys Phe Gly Gly Ser Ser Leu Ala Asp Ala Asp Arg
1               5                   10                  15

Phe Leu Arg Ala Ala Asp Ile Ile Ala Asn Asn Ala Gln Gln Glu Glu
            20                  25                  30

Val Ala Val Val Leu Ser Ala Pro Gly Lys Thr Thr Asn Lys Leu Val
        35                  40                  45

Ala Val Ile Glu Gly Ala Leu Arg Asn Gly Glu Ala Leu Gln Ile
    50                  55                  60

Asn Glu Leu Glu Glu Ser Phe Lys Thr Leu Phe Ala Asp Ile Gln Ala
65                  70                  75                  80

Leu Val Pro Asn Leu Asp Gly Thr Gly Tyr Asp Asn Gln Val Lys Thr
                85                  90                  95

Ser Leu Ser Gln Leu Arg Gln Phe Val His Gly Ile Ser Leu Leu Gly
            100                 105                 110

Met Cys Pro Asn Asn Val Asn Ala Arg Ile Ile Ser Lys Gly Glu Arg
        115                 120                 125

Val Ser Ile Gln Leu Met Lys Ala Val Leu Glu Ala Lys Gly Gln Lys
    130                 135                 140

Ala Ser Leu Ile Asp Pro Val Glu Tyr Leu Tyr Ala Gln Gly Asp His
145                 150                 155                 160

Leu Glu Ala Met Val Asp Val Asp Ile Ser Thr Gln Asn Phe Arg Gln
                165                 170                 175

Lys Pro Leu Pro Gln Gly His Val Asn Ile Met Pro Gly Phe Thr Ala
            180                 185                 190

Gly Asn Glu Lys Gly Glu Leu Val Thr Leu Gly Arg Asn Gly Ser Asp
        195                 200                 205

Tyr Ser Ala Ala Val Leu Ala Ala Cys Leu Arg Ala Asp Cys Cys Glu
    210                 215                 220

Ile Trp Thr Asp Val Asp Gly Val Tyr Asn Cys Asp Pro Arg Leu Val
225                 230                 235                 240

Glu Asp Ala Arg Leu Leu Lys Ser Leu Ser Tyr Gln Glu Ala Met Glu
                245                 250                 255

Leu Ser Tyr Phe Gly Ala Ser Val Leu His Pro Lys Thr Ile Ala Pro
            260                 265                 270
```

```
Ile Ala Gln Phe His Ile Pro Cys Leu Ile Lys Asn Ser Phe Asn Pro
            275                 280                 285

Gln Gly Ala Gly Thr Leu Ile Gly Gln Asp Thr Gly Glu Asp Asn Leu
        290                 295                 300

Ala Ile Lys Gly Ile Thr Thr Leu Asn Asp Leu Thr Met Val Asn Val
305                 310                 315                 320

Ser Gly Pro Gly Met Lys Gly Met Val Gly Met Ala Ser Arg Val Phe
                325                 330                 335

Gly Ala Met Ser Ser Ala Gly Val Ser Ile Val Leu Ile Thr Gln Ser
            340                 345                 350

Ser Ser Glu Tyr Ser Ile Ser Phe Cys Ile Glu Ala Glu Asp Lys Ala
        355                 360                 365

Lys Ala Gln Gln Thr Leu Ala Glu Ala Phe Glu Leu Glu Leu Lys Asp
    370                 375                 380

Gly Leu Leu Glu Pro Val Glu Phe Ile Asp Asp Val Ala Ile Val Thr
385                 390                 395                 400

Leu Val Gly Asp Gly Met Arg Thr Ser Arg Gly Val Ala Ser Arg Phe
                405                 410                 415

Phe Ser Ser Leu Ala Glu Val Asn Val Asn Ile Val Ala Ile Ala Gln
            420                 425                 430

Gly Ser Ser Glu Arg Ala Ile Ser Ala Val Ile Pro Glu Asp Lys Ile
        435                 440                 445

Ser Glu Ala Ile Lys Ala Cys His Met Asn Leu Phe Asn Ser Lys His
    450                 455                 460

Phe Leu Asp Val Phe Val Val Gly Ile Gly Gly Val Gly Gly Glu Leu
465                 470                 475                 480

Val Asp Gln Ile Glu Arg Gln Gln Ala Lys Leu Ala Glu Lys Gly Ile
                485                 490                 495

Ile Ile Arg Val Cys Gly Leu Ala Asn Ser Lys Gly Leu Leu Leu Asp
            500                 505                 510

Ser Glu Gly Leu Pro Leu Glu His Trp Arg Asp Arg Met Ser Ser Ala
        515                 520                 525

Thr Glu Glu Phe Ser Leu Ala Arg Leu Ile Ala Leu Val Gln Arg Asn
    530                 535                 540

His Ile Ile Asn Pro Val Leu Val Asp Cys Thr Ser Ser Glu Ala Ile
545                 550                 555                 560

Ala Asn Gln Tyr Ala Asp Phe Leu Ala Ala Gly Phe His Val Val Thr
                565                 570                 575

Pro Asn Lys Lys Ala Asn Thr Ala Ser Met Ala Tyr Tyr His Gln Leu
            580                 585                 590

Arg Asp Val Ala Arg Ser Ser Arg Arg Lys Leu Met Tyr Glu Thr Thr
        595                 600                 605

Val Gly Ala Gly Leu Pro Val Ile Glu Asn Leu Gln Asn Leu Ile Ser
    610                 615                 620

Ala Gly Asp Glu Leu Glu Arg Phe Thr Gly Ile Leu Ser Gly Ser Leu
625                 630                 635                 640

Ser Tyr Ile Phe Gly Lys Leu Asp Glu Gly Met Ser Leu Ser Glu Ala
                645                 650                 655

Thr Asn Ile Ala Lys Glu Asn Gly Phe Thr Glu Pro Asp Pro Arg Asp
            660                 665                 670

Asp Leu Ser Gly Met Asp Val Ala Arg Lys Leu Leu Ile Leu Ala Arg
        675                 680                 685

Glu Ala Gly Met Ser Leu Glu Leu Glu Asp Val Val Val Asp Gln Ala
```

```
                690                 695                 700
Leu Pro Pro Gly Phe Asp Asp Ser Gly Ser Val Asp Glu Phe Met Ala
705                 710                 715                 720

Arg Leu Pro Glu Ala Asp Ala Tyr Phe Lys Asp Leu Val Ala Lys Ala
                725                 730                 735

Ala Glu Glu Gly Lys Val Leu Arg Tyr Val Gly Glu Ile Asn Asp Gly
                740                 745                 750

Lys Cys Lys Val Ser Ile Ala Ile Val Asp Glu Asn Asp Pro Met Phe
                755                 760                 765

Lys Ile Lys Asp Gly Glu Asn Ala Leu Ala Phe Tyr Ser Arg Tyr Tyr
                770                 775                 780

Gln Pro Ile Pro Leu Val Leu Arg Gly Tyr Gly Ala Gly Thr Glu Val
785                 790                 795                 800

Thr Ala Ala Gly Val Phe Ser Asp Val Met Arg Thr Leu Gly Trp Lys
                805                 810                 815

Leu Gly Val

<210> SEQ ID NO 25
<211> LENGTH: 3214
<212> TYPE: DNA
<213> ORGANISM: Vibrio natriegens
<220> FEATURE:
<221> NAME/KEY: CDS
<222> LOCATION: (376)..(2781)

<400> SEQUENCE: 25
ctgcagaagc aatctttggt ggcgaaaatt tatcatccaa gtcttccaca gcaccctggc    60
catgagattg ctaaaaagca acagtctggt tttggctcta tgttgagctt tgagtttgcg   120
ggctcgtttg agcagcttaa agcctttgtc aaagagcttc agttgttctc acttgcagag   180
tctctgggcg gggtagaaag cttgatttgt cacccagcat ctatgacgca tcgcgcgatg   240
ggtgaagaag ccttggctga gcgggtgta tcacagcaat tgctgcgcct ttctgtaggg    300
ctagaagatg cacaagatct tattgccgac ctagaacaag cattcactaa atctgcacag   360
caataggagt taata atg act gta caa cgt cag cta cac aag ttt ggt ggt   411
                 Met Thr Val Gln Arg Gln Leu His Lys Phe Gly Gly
                 1               5                   10 agc agc ctg gca aac cca gag tgt tac tta cgt gta gcg gga att ctc   459
Ser Ser Leu Ala Asn Pro Glu Cys Tyr Leu Arg Val Ala Gly Ile Leu
        15                  20                  25 aag gaa tac tct gca gaa aat gac ttg gtg gtg gtc tct gca gca ggt   507
Lys Glu Tyr Ser Ala Glu Asn Asp Leu Val Val Val Ser Ala Ala Gly
30                  35                  40 aaa aca acc aac cgc ctg att gag ttc ctt gaa ggc tta gaa aaa gat   555
Lys Thr Thr Asn Arg Leu Ile Glu Phe Leu Glu Gly Leu Glu Lys Asp
45                  50                  55                  60 gga cga att gcg cac gaa gct ttg cag agc ttg aga cag ttt caa atc   603
Gly Arg Ile Ala His Glu Ala Leu Gln Ser Leu Arg Gln Phe Gln Ile
                65                  70                  75 agt ctc att gaa gag tta tta gag gga gac gcg caa gaa cag ctg ctt   651
Ser Leu Ile Glu Glu Leu Leu Glu Gly Asp Ala Gln Glu Gln Leu Leu
        80                  85                  90 gcc tcc tta caa gat gaa ttc agt aca tta gcg gaa ctg acc tct ccg   699
Ala Ser Leu Gln Asp Glu Phe Ser Thr Leu Ala Glu Leu Thr Ser Pro
    95                  100                 105 ctg acc gaa gcg caa aag gcg gcg gta tta ggc cac gga gaa gta tgg   747
Leu Thr Glu Ala Gln Lys Ala Ala Val Leu Gly His Gly Glu Val Trp
110                 115                 120
```

```
tct tct cga tta ctg gcc gct tta ctg acg caa aag caa ctg cct gct    795
Ser Ser Arg Leu Leu Ala Ala Leu Leu Thr Gln Lys Gln Leu Pro Ala
125                 130                 135                 140 gta gcg caa gat gcg cga gca ttc cta cgc gca gaa gcg ggc act caa    843
Val Ala Gln Asp Ala Arg Ala Phe Leu Arg Ala Glu Ala Gly Thr Gln
            145                 150                 155 cca gaa gtt gat cgt gct cgt tca tat ccg ctt atc aaa gag gca ctg    891
Pro Glu Val Asp Arg Ala Arg Ser Tyr Pro Leu Ile Lys Glu Ala Leu
        160                 165                 170 gca caa cat agc cac aaa cgt gtg atc att acc ggc ttc atg gca caa    939
Ala Gln His Ser His Lys Arg Val Ile Ile Thr Gly Phe Met Ala Gln
    175                 180                 185 aac gat aac ggt gaa act gtt ctg ctt ggc cgc aac ggt tca gac tac    987
Asn Asp Asn Gly Glu Thr Val Leu Leu Gly Arg Asn Gly Ser Asp Tyr
190                 195                 200 tct gca acc gta att ggt gcg ctt gca gaa gtg agc aca gtg acg att   1035
Ser Ala Thr Val Ile Gly Ala Leu Ala Glu Val Ser Thr Val Thr Ile
205                 210                 215                 220 tgg agt gat gtg gct ggt gtt tat agc gca gac cct cgt ttg gta tca   1083
Trp Ser Asp Val Ala Gly Val Tyr Ser Ala Asp Pro Arg Leu Val Ser
            225                 230                 235 gat gca tgt tta cta cct ctc tta agg ctg gat gaa gcg agt gag ctg   1131
Asp Ala Cys Leu Leu Pro Leu Leu Arg Leu Asp Glu Ala Ser Glu Leu
        240                 245                 250 gct cgt tta gct gcg cca gtt ctg cac agc cga acc ttg cag cct gtg   1179
Ala Arg Leu Ala Ala Pro Val Leu His Ser Arg Thr Leu Gln Pro Val
    255                 260                 265 gct caa agc acc atg gat ctg agc ctt aaa tgc agt tac ctg cca gag   1227
Ala Gln Ser Thr Met Asp Leu Ser Leu Lys Cys Ser Tyr Leu Pro Glu
270                 275                 280 tca ggt tcg acc cgc att gag cga gtt ctg gct tct ggt cgc ggg gcg   1275
Ser Gly Ser Thr Arg Ile Glu Arg Val Leu Ala Ser Gly Arg Gly Ala
285                 290                 295                 300 aaa atc atc acc tca ctg gat gac gtg cta ttg gtt cag cta gca ttt   1323
Lys Ile Ile Thr Ser Leu Asp Asp Val Leu Leu Val Gln Leu Ala Phe
            305                 310                 315 gcg cat gga cat gac ttt gag aaa gca cag agt gat gtt ctg gaa tcc   1371
Ala His Gly His Asp Phe Glu Lys Ala Gln Ser Asp Val Leu Glu Ser
        320                 325                 330 cta aaa cgc gtt cag ttg gag cca ctg gca ttt gaa gct cag cct gaa   1419
Leu Lys Arg Val Gln Leu Glu Pro Leu Ala Phe Glu Ala Gln Pro Glu
    335                 340                 345 cag cag ata tta cga ctg gca tac aca gca gaa att gct ggc ggt gca   1467
Gln Gln Ile Leu Arg Leu Ala Tyr Thr Ala Glu Ile Ala Gly Gly Ala
350                 355                 360 ctc aag tat cta cag gaa tct gat ctg gat gcg gag att aac ctc act   1515
Leu Lys Tyr Leu Gln Glu Ser Asp Leu Asp Ala Glu Ile Asn Leu Thr
365                 370                 375                 380 gat ggt tac tct ctg att gct gcc gta ggt gct ggt gtg aca act aat   1563
Asp Gly Tyr Ser Leu Ile Ala Ala Val Gly Ala Gly Val Thr Thr Asn
            385                 390                 395 gcc aac cac tgt ttt ggt ttt cag caa aag ctg aaa cac tct ccg gtg   1611
Ala Asn His Cys Phe Gly Phe Gln Gln Lys Leu Lys His Ser Pro Val
        400                 405                 410 gaa ttt atc gct gag acg gag tct ggt tta agt ctg gtc gca gta tta   1659
Glu Phe Ile Ala Glu Thr Glu Ser Gly Leu Ser Leu Val Ala Val Leu
    415                 420                 425 cgt aac act gat acc gaa gaa ctg gta cag acg gtt cac agc cag tta   1707
Arg Asn Thr Asp Thr Glu Glu Leu Val Gln Thr Val His Ser Gln Leu
```

```
              430             435             440
ttt cag gca cag aag cgc gtt gct gtc gca tta tgc ggg aaa ggg aat    1755
Phe Gln Ala Gln Lys Arg Val Ala Val Ala Leu Cys Gly Lys Gly Asn
445             450             455             460 atc ggt tcg agc tgg ctg agt tta ttc gct tca cag aag aat gaa ctt    1803
Ile Gly Ser Ser Trp Leu Ser Leu Phe Ala Ser Gln Lys Asn Glu Leu
            465             470             475 gaa aaa cgt cat ggc atg agc ttt gac tta gtc gcg gtg gtt gat agc    1851
Glu Lys Arg His Gly Met Ser Phe Asp Leu Val Ala Val Val Asp Ser
        480             485             490 caa atg tat tgg ttt gat agc caa ggc att gat gca tcc agt gtt tca    1899
Gln Met Tyr Trp Phe Asp Ser Gln Gly Ile Asp Ala Ser Ser Val Ser
    495             500             505 gca cgc ttc aat gac gaa agt atc gca aac gat ggc tct tgg tta tct    1947
Ala Arg Phe Asn Asp Glu Ser Ile Ala Asn Asp Gly Ser Trp Leu Ser
510             515             520 cgt ctt ggt gct ttg cag gac tac gat gaa gct gtg gtc ctc gat gtt    1995
Arg Leu Gly Ala Leu Gln Asp Tyr Asp Glu Ala Val Val Leu Asp Val
525             530             535             540 acc gcc agt cag gaa tta gcg aaa tgt tac gtt gat atc gct cag caa    2043
Thr Ala Ser Gln Glu Leu Ala Lys Cys Tyr Val Asp Ile Ala Gln Gln
            545             550             555 ggt att cac cta att tca gcg aat aaa gtc gca ggt tca gct gat agt    2091
Gly Ile His Leu Ile Ser Ala Asn Lys Val Ala Gly Ser Ala Asp Ser
        560             565             570 cag tat tac cat cag gtc cag gat gcg ttt gcc aaa att gga cgt cac    2139
Gln Tyr Tyr His Gln Val Gln Asp Ala Phe Ala Lys Ile Gly Arg His
    575             580             585 tgg ctg tat aac gct acg gta ggt gcc ggg tta cca atc aac cat acg    2187
Trp Leu Tyr Asn Ala Thr Val Gly Ala Gly Leu Pro Ile Asn His Thr
590             595             600 gtg cgc gat ctt cgt gag agt ggt gat gag att att gca ctc tct ggt    2235
Val Arg Asp Leu Arg Glu Ser Gly Asp Glu Ile Ile Ala Leu Ser Gly
605             610             615             620 att ttc tcc ggt acg ctt tca tgg tta ttc caa cag ttt gat ggc tca    2283
Ile Phe Ser Gly Thr Leu Ser Trp Leu Phe Gln Gln Phe Asp Gly Ser
            625             630             635 gtg cca ttc agc gag tta gtg gat tta gcc tgg cag caa gga tta aca    2331
Val Pro Phe Ser Glu Leu Val Asp Leu Ala Trp Gln Gln Gly Leu Thr
        640             645             650 gaa cct gac cct cgc tct gac tta gat ggc tct gat gtg atg cgt aag    2379
Glu Pro Asp Pro Arg Ser Asp Leu Asp Gly Ser Asp Val Met Arg Lys
    655             660             665 ctg gtt att ctg gcg cgt gag tct ggt ctg gac atc gag ccg gga agc    2427
Leu Val Ile Leu Ala Arg Glu Ser Gly Leu Asp Ile Glu Pro Gly Ser
670             675             680 gta aag gta gag tcg tta gtt cct gaa gaa ctg cgc acg ctc agc tta    2475
Val Lys Val Glu Ser Leu Val Pro Glu Glu Leu Arg Thr Leu Ser Leu
685             690             695             700 gat gag ttt ttt gat aac gcc gca ctg ctg agc cag act ctg caa gaa    2523
Asp Glu Phe Phe Asp Asn Ala Ala Leu Leu Ser Gln Thr Leu Gln Glu
            705             710             715 cgt ttg tcc aaa gcg cag aaa aac gat cag gta ctg cgt tac gtt gcg    2571
Arg Leu Ser Lys Ala Gln Lys Asn Asp Gln Val Leu Arg Tyr Val Ala
        720             725             730 cgt tta gag aaa gat ggc aaa gcg acc gtc ggc att gaa gcc ttg tcc    2619
Arg Leu Glu Lys Asp Gly Lys Ala Thr Val Gly Ile Glu Ala Leu Ser
    735             740             745 cgt gag cat gcg ctg gct aac cta ctg ccg tgt gac aat att ttt gct    2667
```

```
Arg Glu His Ala Leu Ala Asn Leu Leu Pro Cys Asp Asn Ile Phe Ala
            750                 755                 760 att gag agc aag tgg tac aaa gac aac ccg ctt gtt atc cgc ggt cct    2715
Ile Glu Ser Lys Trp Tyr Lys Asp Asn Pro Leu Val Ile Arg Gly Pro
765                 770                 775                 780 ggc gct gga cgt gaa gtt acg gca ggg gcg att cag tcc gat tta aac    2763
Gly Ala Gly Arg Glu Val Thr Ala Gly Ala Ile Gln Ser Asp Leu Asn
                785                 790                 795 cgc ctt gct ggg cta ttc taaacactca aaccccgga attcatccgg            2811
Arg Leu Ala Gly Leu Phe
                800 ggttttttat tcctgtcttg gtgccataat taatctcaga accgttattg gcgaactatt  2871 tttgtggata aatattagcc aacaatcaac ttgaactatc ctcatcatta acgtgaaaaa  2931 aattcataat cacaaggttg acattaaatc gtattcaata cattctgtag acatatagac  2991 gtctaaacgt cgatttgaga atttgatttc gtggcgggtt gccacaggga gagtaagatg  3051 ggttacacgc acgcaggcca tatcgatgcc ttaaaccaga atatcgctga attgtcagac  3111 aatattaatg tttcatttga gttttttccg ccaagcaatg aaaagatgga agagacgcta  3171 tggaactctg tgcaccgtct aaaaacactc aagcctaagt ttg                   3214
```

<210> SEQ ID NO 26
<211> LENGTH: 802
<212> TYPE: PRT
<213> ORGANISM: Vibrio natriegens

<400> SEQUENCE: 26

```
Met Thr Val Gln Arg Gln Leu His Lys Phe Gly Gly Ser Ser Leu Ala
1               5                   10                  15

Asn Pro Glu Cys Tyr Leu Arg Val Ala Gly Ile Leu Lys Glu Tyr Ser
            20                  25                  30

Ala Glu Asn Asp Leu Val Val Val Ser Ala Ala Gly Lys Thr Thr Asn
        35                  40                  45

Arg Leu Ile Glu Phe Leu Glu Gly Leu Glu Lys Asp Gly Arg Ile Ala
    50                  55                  60

His Glu Ala Leu Gln Ser Leu Arg Gln Phe Gln Ile Ser Leu Ile Glu
65                  70                  75                  80

Glu Leu Leu Glu Gly Asp Ala Gln Glu Gln Leu Leu Ala Ser Leu Gln
                85                  90                  95

Asp Glu Phe Ser Thr Leu Ala Glu Leu Thr Ser Pro Leu Thr Glu Ala
            100                 105                 110

Gln Lys Ala Ala Val Leu Gly His Gly Glu Val Trp Ser Ser Arg Leu
        115                 120                 125

Leu Ala Ala Leu Leu Thr Gln Lys Gln Leu Pro Ala Val Ala Gln Asp
    130                 135                 140

Ala Arg Ala Phe Leu Arg Ala Glu Ala Gly Thr Gln Pro Glu Val Asp
145                 150                 155                 160

Arg Ala Arg Ser Tyr Pro Leu Ile Lys Glu Ala Leu Ala Gln His Ser
                165                 170                 175

His Lys Arg Val Ile Ile Thr Gly Phe Met Ala Gln Asn Asp Asn Gly
            180                 185                 190

Glu Thr Val Leu Leu Gly Arg Asn Gly Ser Asp Tyr Ser Ala Thr Val
        195                 200                 205

Ile Gly Ala Leu Ala Glu Val Ser Thr Val Thr Ile Trp Ser Asp Val
    210                 215                 220
```

```
Ala Gly Val Tyr Ser Ala Asp Pro Arg Leu Val Ser Asp Ala Cys Leu
225                 230                 235                 240

Leu Pro Leu Leu Arg Leu Asp Glu Ala Ser Glu Leu Ala Arg Leu Ala
            245                 250                 255

Ala Pro Val Leu His Ser Arg Thr Leu Gln Pro Val Ala Gln Ser Thr
        260                 265                 270

Met Asp Leu Ser Leu Lys Cys Ser Tyr Leu Pro Glu Ser Gly Ser Thr
            275                 280                 285

Arg Ile Glu Arg Val Leu Ala Ser Gly Arg Gly Ala Lys Ile Ile Thr
290                 295                 300

Ser Leu Asp Asp Val Leu Leu Val Gln Leu Ala Phe Ala His Gly His
305                 310                 315                 320

Asp Phe Glu Lys Ala Gln Ser Asp Val Leu Glu Ser Leu Lys Arg Val
            325                 330                 335

Gln Leu Glu Pro Leu Ala Phe Glu Ala Gln Pro Glu Gln Gln Ile Leu
            340                 345                 350

Arg Leu Ala Tyr Thr Ala Glu Ile Ala Gly Gly Ala Leu Lys Tyr Leu
            355                 360                 365

Gln Glu Ser Asp Leu Asp Ala Glu Ile Asn Leu Thr Asp Gly Tyr Ser
370                 375                 380

Leu Ile Ala Ala Val Gly Ala Gly Val Thr Thr Asn Ala Asn His Cys
385                 390                 395                 400

Phe Gly Phe Gln Gln Lys Leu Lys His Ser Pro Val Glu Phe Ile Ala
            405                 410                 415

Glu Thr Glu Ser Gly Leu Ser Leu Val Ala Val Leu Arg Asn Thr Asp
            420                 425                 430

Thr Glu Glu Leu Val Gln Thr Val His Ser Gln Leu Phe Gln Ala Gln
            435                 440                 445

Lys Arg Val Ala Val Ala Leu Cys Gly Lys Gly Asn Ile Gly Ser Ser
450                 455                 460

Trp Leu Ser Leu Phe Ala Ser Gln Lys Asn Glu Leu Glu Lys Arg His
465                 470                 475                 480

Gly Met Ser Phe Asp Leu Val Ala Val Val Asp Ser Gln Met Tyr Trp
            485                 490                 495

Phe Asp Ser Gln Gly Ile Asp Ala Ser Ser Val Ser Ala Arg Phe Asn
            500                 505                 510

Asp Glu Ser Ile Ala Asn Asp Gly Ser Trp Leu Ser Arg Leu Gly Ala
            515                 520                 525

Leu Gln Asp Tyr Asp Glu Ala Val Val Leu Asp Val Thr Ala Ser Gln
530                 535                 540

Glu Leu Ala Lys Cys Tyr Val Asp Ile Ala Gln Gln Gly Ile His Leu
545                 550                 555                 560

Ile Ser Ala Asn Lys Val Ala Gly Ser Ala Asp Ser Gln Tyr Tyr His
            565                 570                 575

Gln Val Gln Asp Ala Phe Ala Lys Ile Gly Arg His Trp Leu Tyr Asn
            580                 585                 590

Ala Thr Val Gly Ala Gly Leu Pro Ile Asn His Thr Val Arg Asp Leu
            595                 600                 605

Arg Glu Ser Gly Asp Glu Ile Ile Ala Leu Ser Gly Ile Phe Ser Gly
            610                 615                 620

Thr Leu Ser Trp Leu Phe Gln Gln Phe Asp Gly Ser Val Pro Phe Ser
625                 630                 635                 640

Glu Leu Val Asp Leu Ala Trp Gln Gln Gly Leu Thr Glu Pro Asp Pro
```

```
                645                 650                 655
Arg Ser Asp Leu Asp Gly Ser Asp Val Met Arg Lys Leu Val Ile Leu
            660                 665                 670

Ala Arg Glu Ser Gly Leu Asp Ile Glu Pro Gly Ser Val Lys Val Glu
            675                 680                 685

Ser Leu Val Pro Glu Glu Leu Arg Thr Leu Ser Leu Asp Glu Phe Phe
            690                 695                 700

Asp Asn Ala Ala Leu Leu Ser Gln Thr Leu Gln Glu Arg Leu Ser Lys
705                 710                 715                 720

Ala Gln Lys Asn Asp Gln Val Leu Arg Tyr Val Ala Arg Leu Glu Lys
            725                 730                 735

Asp Gly Lys Ala Thr Val Gly Ile Glu Ala Leu Ser Arg Glu His Ala
            740                 745                 750

Leu Ala Asn Leu Leu Pro Cys Asp Asn Ile Phe Ala Ile Glu Ser Lys
            755                 760                 765

Trp Tyr Lys Asp Asn Pro Leu Val Ile Arg Gly Pro Gly Ala Gly Arg
            770                 775                 780

Glu Val Thr Ala Gly Ala Ile Gln Ser Asp Leu Asn Arg Leu Ala Gly
785                 790                 795                 800

Leu Phe

<210> SEQ ID NO 27
<211> LENGTH: 2648
<212> TYPE: DNA
<213> ORGANISM: Vibrio natriegens
<220> FEATURE:
<221> NAME/KEY: misc_feature
<222> LOCATION: (862)
<223> OTHER INFORMATION: n = a, t, g or c
<220> FEATURE:
<221> NAME/KEY: CDS
<222> LOCATION: (1060)..(2409)

<400> SEQUENCE: 27
ataactacgg ccagtgccaa gcttgcatgc ctgcaggtcg actctagagg atcccttgt      60 gttgcttggc taacttaccc aaagcttgag cgtcgctgac cgcacctgtc gatgtttccg    120
cgtgaacaaa tgctaaaatt tttgtgtcag gatgctgctg cagtgcttgt tcgactttat    180
cgacagagac tggcgcgccc cactcgtcat caaccaagac aacttcacca ccagcacgaa    240
caacgttttc acgcatgcgc tcaccaaaaa caccatttcg gcatacgata actttgtcac    300
ctttctcgat aaggttaaca aaacatgcct ccatacccgc actacctgga gcagaaacgg    360
caatagtaaa gtcgttttct gtctggaacg cgtactttag caattgtttc agctcatcca    420
tcattgcgat aaacagaggg tccaagtgac caaccgttgg gcggctaagc gcttgcagca    480
cttgcggata gatatctgaa ggacctggtc ccattagggt acggtgaggg ggaataaagc    540
tttggatcgg catgtgagct ccttgtttga cgttacttaa cccgagcgcg acaatagtt    600 tttagaattt tgaataagtc tcgggcatca agaactcac actaatggat tttatagtgc    660
tcggcaatta gccgtaggta ttgagttcaa accactgtca caatttcact aataaaaaat    720
cttgaaatag ttgaaatatt cattgacttt gtgacgccaa aaccgttcaa tgtttgagct    780
ttatgtggaa gaggagcact acccaggtag ataatttgtg gaaccgcaat tccaatacga    840
attattcagg gggagtagtg cncgaggtaa gtcaaatttg cagggtttga cttgtcggtt    900
gacgtgggtt gagtcccatc aactgtcatc agcattgtct gatgaagagc ttctgagggt    960
acatatttca aatatcactc taaatacctc tcttttgct ctgttccttt cctcactaaa    1020
```

```
tatcggatat attagtttaa gaagtcgtgg gagaactca gtg agc gca ttt aac        1074
                                            Val Ser Ala Phe Asn
                                             1               5 gta gca aaa ttc ggt gga acc agt gtt gcc aat ttc gag gca atg agc      1122
Val Ala Lys Phe Gly Gly Thr Ser Val Ala Asn Phe Glu Ala Met Ser
             10                  15                  20 cgt tgt gcc gcc att att gaa aac aat cca aat act cgc ctt gtc gtt      1170
Arg Cys Ala Ala Ile Ile Glu Asn Asn Pro Asn Thr Arg Leu Val Val
             25                  30                  35 agc agc gct tgc tct ggt gta acg aac cta ttg gta gaa ctg gcc aat      1218
Ser Ser Ala Cys Ser Gly Val Thr Asn Leu Leu Val Glu Leu Ala Asn
             40                  45                  50 ggt gtt cag gat cag gaa cag cgt gcc gag ttg cta cgt aag cta gca      1266
Gly Val Gln Asp Gln Glu Gln Arg Ala Glu Leu Leu Arg Lys Leu Ala
         55                  60                  65 gaa att cat gat gac atc ctt agt caa cta aga gat gca gca gaa gca      1314
Glu Ile His Asp Asp Ile Leu Ser Gln Leu Arg Asp Ala Ala Glu Ala
70                  75                  80                  85 agt gca gag gtt tac gca atc ctt gat acg gta acc agc ctt gca gaa      1362
Ser Ala Glu Val Tyr Ala Ile Leu Asp Thr Val Thr Ser Leu Ala Glu
                 90                  95                 100 gca gct tct atc caa gct agc tct aaa ctg aca gac cat tta gtt gcg      1410
Ala Ala Ser Ile Gln Ala Ser Ser Lys Leu Thr Asp His Leu Val Ala
            105                 110                 115 tgt ggt gag tta atg tcg acg cac att ttg gct caa ctg atg aga gag      1458
Cys Gly Glu Leu Met Ser Thr His Ile Leu Ala Gln Leu Met Arg Glu
            120                 125                 130 cgt ggt atc aat gcg gtg cgt ttt gat att cgt gat gtg cta aga acc      1506
Arg Gly Ile Asn Ala Val Arg Phe Asp Ile Arg Asp Val Leu Arg Thr
        135                 140                 145 gac gat aac ttc gga cgt gct gag cca aat gtc gaa gcg att tct cag      1554
Asp Asp Asn Phe Gly Arg Ala Glu Pro Asn Val Glu Ala Ile Ser Gln
150                 155                 160                 165 cta gct caa gag aag tta gtc cct cta tgt cag gag tca gta gtc att      1602
Leu Ala Gln Glu Lys Leu Val Pro Leu Cys Gln Glu Ser Val Val Ile
                170                 175                 180 act caa ggc ttc atc ggc tca gac gaa gaa ggc aat aca acc aca tta      1650
Thr Gln Gly Phe Ile Gly Ser Asp Glu Glu Gly Asn Thr Thr Thr Leu
            185                 190                 195 ggt cgt ggt ggc agt gac tac agt gcc gca ctc att gct gaa ggc gtt      1698
Gly Arg Gly Gly Ser Asp Tyr Ser Ala Ala Leu Ile Ala Glu Gly Val
            200                 205                 210 aaa gct tct ggt tta gaa atc tgg act gat gtt ccg ggc atc tac aca      1746
Lys Ala Ser Gly Leu Glu Ile Trp Thr Asp Val Pro Gly Ile Tyr Thr
        215                 220                 225 aca gac cca cgt att gcg cca aaa gcg tct cct att cca gag atc agc      1794
Thr Asp Pro Arg Ile Ala Pro Lys Ala Ser Pro Ile Pro Glu Ile Ser
230                 235                 240                 245 ttt agc gaa gcg tca gaa atg gca aac ttc ggt gct aag atc ctc cac      1842
Phe Ser Glu Ala Ser Glu Met Ala Asn Phe Gly Ala Lys Ile Leu His
                250                 255                 260 cct tct aca ctc gtt cct gct ttg cgc cac gac att cca gtg ttt gtt      1890
Pro Ser Thr Leu Val Pro Ala Leu Arg His Asp Ile Pro Val Phe Val
            265                 270                 275 ggc tct tct aaa gat cca gaa gca ggt ggc aca tgg att cgt cac caa      1938
Gly Ser Ser Lys Asp Pro Glu Ala Gly Gly Thr Trp Ile Arg His Gln
            280                 285                 290 gta gaa agc tcg ccg cta tac cga gct ctt gca ttg cgt tgc aac caa      1986
Val Glu Ser Ser Pro Leu Tyr Arg Ala Leu Ala Leu Arg Cys Asn Gln
```

```
                    295                 300                 305
acc atg gtc act cta cgt agt gca agc atg ttc cat gca tac ggc ttc       2034
Thr Met Val Thr Leu Arg Ser Ala Ser Met Phe His Ala Tyr Gly Phe
310                 315                 320                 325 ctg gct aaa gtg ttc gag att ctg gct aaa cac aaa att tca gtg gac       2082
Leu Ala Lys Val Phe Glu Ile Leu Ala Lys His Lys Ile Ser Val Asp
                330                 335                 340 ctg att acc act tca gaa atc agt gtt tcg tta act cta gac caa aca       2130
Leu Ile Thr Thr Ser Glu Ile Ser Val Ser Leu Thr Leu Asp Gln Thr
            345                 350                 355 gac acc tct ggt ggt gca cca caa cta cct caa gcc gta aga gaa gag       2178
Asp Thr Ser Gly Gly Ala Pro Gln Leu Pro Gln Ala Val Arg Glu Glu
        360                 365                 370 cta gaa gaa ttg tgt aaa gtg gaa gta gag cac gac cta tgc ttg gtg       2226
Leu Glu Glu Leu Cys Lys Val Glu Val Glu His Asp Leu Cys Leu Val
    375                 380                 385 gct ctt atc gga aac aac atg agc ggt agc aaa gga tac gcc aaa caa       2274
Ala Leu Ile Gly Asn Asn Met Ser Gly Ser Lys Gly Tyr Ala Lys Gln
390                 395                 400                 405 gta ttc ggt aca tta gaa gac ttt aac ctg cgt atg att tgc tac ggt       2322
Val Phe Gly Thr Leu Glu Asp Phe Asn Leu Arg Met Ile Cys Tyr Gly
                410                 415                 420 gcg agc ccg cat aac ttg tgc ttc cta ctg cac aag tca gaa tcg caa       2370
Ala Ser Pro His Asn Leu Cys Phe Leu Leu His Lys Ser Glu Ser Gln
            425                 430                 435 cag gcg att caa aaa ctg cat gct gag cta ttt gaa aaa taaacgctgt        2419
Gln Ala Ile Gln Lys Leu His Ala Glu Leu Phe Glu Lys
        440                 445                 450 tcatctcaca atataaaaag gctgcctga tggcagccct ttctctttcc gttggattag      2479
ccgttaatat tcggacctaa ccattttct gcttcaagcc tgtcccaacc tttacgttca      2539
gcatagcttt ctaactgatc ttcctggatc tgcgcgatcg caaagtagcg agaatccgga     2599
tgagagaagt accaaccaga cactgaggca ccagggtaca tggcataga                 2648

<210> SEQ ID NO 28
<211> LENGTH: 450
<212> TYPE: PRT
<213> ORGANISM: Vibrio natriegens

<400> SEQUENCE: 28

Val Ser Ala Phe Asn Val Ala Lys Phe Gly Gly Thr Ser Val Ala Asn
1               5                   10                  15

Phe Glu Ala Met Ser Arg Cys Ala Ala Ile Ile Glu Asn Asn Pro Asn
                20                  25                  30

Thr Arg Leu Val Val Ser Ser Ala Cys Ser Gly Val Thr Asn Leu Leu
            35                  40                  45

Val Glu Leu Ala Asn Gly Val Gln Asp Gln Glu Gln Arg Ala Glu Leu
        50                  55                  60

Leu Arg Lys Leu Ala Glu Ile His Asp Asp Ile Leu Ser Gln Leu Arg
65                  70                  75                  80

Asp Ala Ala Glu Ala Ser Ala Glu Val Tyr Ala Ile Leu Asp Thr Val
                85                  90                  95

Thr Ser Leu Ala Glu Ala Ala Ser Ile Gln Ala Ser Ser Lys Leu Thr
            100                 105                 110

Asp His Leu Val Ala Cys Gly Glu Leu Met Ser Thr His Ile Leu Ala
        115                 120                 125

Gln Leu Met Arg Glu Arg Gly Ile Asn Ala Val Arg Phe Asp Ile Arg
```

```
                    130                 135                 140
Asp Val Leu Arg Thr Asp Asp Asn Phe Gly Arg Ala Glu Pro Asn Val
145                 150                 155                 160

Glu Ala Ile Ser Gln Leu Ala Gln Glu Lys Leu Val Pro Leu Cys Gln
                165                 170                 175

Glu Ser Val Val Ile Thr Gln Gly Phe Ile Gly Ser Asp Glu Gly
            180                 185                 190

Asn Thr Thr Thr Leu Gly Arg Gly Gly Ser Asp Tyr Ser Ala Ala Leu
            195                 200                 205

Ile Ala Glu Gly Val Lys Ala Ser Gly Leu Glu Ile Trp Thr Asp Val
210                 215                 220

Pro Gly Ile Tyr Thr Thr Asp Pro Arg Ile Ala Pro Lys Ala Ser Pro
225                 230                 235                 240

Ile Pro Glu Ile Ser Phe Ser Glu Ala Ser Glu Met Ala Asn Phe Gly
            245                 250                 255

Ala Lys Ile Leu His Pro Ser Thr Leu Val Pro Ala Leu Arg His Asp
            260                 265                 270

Ile Pro Val Phe Val Gly Ser Ser Lys Asp Pro Glu Ala Gly Gly Thr
            275                 280                 285

Trp Ile Arg His Gln Val Glu Ser Ser Pro Leu Tyr Arg Ala Leu Ala
290                 295                 300

Leu Arg Cys Asn Gln Thr Met Val Thr Leu Arg Ser Ala Ser Met Phe
305                 310                 315                 320

His Ala Tyr Gly Phe Leu Ala Lys Val Phe Glu Ile Leu Ala Lys His
            325                 330                 335

Lys Ile Ser Val Asp Leu Ile Thr Thr Ser Glu Ile Ser Val Ser Leu
            340                 345                 350

Thr Leu Asp Gln Thr Asp Thr Ser Gly Gly Ala Pro Gln Leu Pro Gln
            355                 360                 365

Ala Val Arg Glu Glu Leu Glu Glu Leu Cys Lys Val Glu Val Glu His
370                 375                 380

Asp Leu Cys Leu Val Ala Leu Ile Gly Asn Asn Met Ser Gly Ser Lys
385                 390                 395                 400

Gly Tyr Ala Lys Gln Val Phe Gly Thr Leu Glu Asp Phe Asn Leu Arg
                405                 410                 415

Met Ile Cys Tyr Gly Ala Ser Pro His Asn Leu Cys Phe Leu Leu His
                420                 425                 430

Lys Ser Glu Ser Gln Gln Ala Ile Gln Lys Leu His Ala Glu Leu Phe
            435                 440                 445

Glu Lys
    450

<210> SEQ ID NO 29
<211> LENGTH: 2331
<212> TYPE: DNA
<213> ORGANISM: Vibrio natriegens
<220> FEATURE:
<221> NAME/KEY: CDS
<222> LOCATION: (344)..(1765)

<400> SEQUENCE: 29
acggaacacg cacatccact acaaaaacca cttagagtca gttttctgta tgagtggtga      60
aggcgagatt gaagtggtag gtggtgaaac ctatccaatc aaaccaggta cactgtacat     120
tctggataaa aacgacgagc actacctaag agcatataaa aacaaagaaa tggtaatggc     180
```

```
gtgcgtattc aacccaccta tcacaggtgc ggaagtacac gatgagaacg gcgtgtaccc    240
tcttgttgac taaaactaaa tagtcactgt gaggtgggct tccacctcac atttcaattc    300
tctcttcttt atttttaag ttaccaatca aaaaggctt aac atg act ttt acc        355
                                                Met Thr Phe Thr
                                                 1 gta gaa aaa atc ggc ggt act tca atg aca gca ttt gat gct gtt cta     403
Val Glu Lys Ile Gly Gly Thr Ser Met Thr Ala Phe Asp Ala Val Leu
 5          10              15              20 gac aat att att ctt cgt ccc aag aca cca tac aac cga gta ttt gtt     451
Asp Asn Ile Ile Leu Arg Pro Lys Thr Pro Tyr Asn Arg Val Phe Val
            25              30              35 gta tcg gcg tac ggt ggt atg act gac gcg cta tta gaa tgt aaa aaa     499
Val Ser Ala Tyr Gly Gly Met Thr Asp Ala Leu Leu Glu Cys Lys Lys
        40              45              50 acc agt aaa gcg ggc gta tac caa ctg gtt gct aag cgt gat gac tcg     547
Thr Ser Lys Ala Gly Val Tyr Gln Leu Val Ala Lys Arg Asp Asp Ser
    55              60              65 tgg gaa gaa gcg ttg gca tac gta gag aat cgt atg ttg ctg aca aac     595
Trp Glu Glu Ala Leu Ala Tyr Val Glu Asn Arg Met Leu Leu Thr Asn
70              75              80 gag aat att ttc gcc gat cca atg aat cga atg cga gcg gat aag ttt     643
Glu Asn Ile Phe Ala Asp Pro Met Asn Arg Met Arg Ala Asp Lys Phe
85              90              95             100 att cgt tca cgc att tca gaa gcg aaa aac tgt atc gct aat att tta     691
Ile Arg Ser Arg Ile Ser Glu Ala Lys Asn Cys Ile Ala Asn Ile Leu
            105             110             115 gaa acg tgc cag tac ggc cag ttt tca ctg cgt cac tac ttg cct caa     739
Glu Thr Cys Gln Tyr Gly Gln Phe Ser Leu Arg His Tyr Leu Pro Gln
        120             125             130 atc cgt gag ttt ctt tct tca att ggt gaa gcg cac agt gct tat aac     787
Ile Arg Glu Phe Leu Ser Ser Ile Gly Glu Ala His Ser Ala Tyr Asn
    135             140             145 acc gcg ttg aaa ctg aaa aac atg ggc att aac gct aag ttt gtc gac     835
Thr Ala Leu Lys Leu Lys Asn Met Gly Ile Asn Ala Lys Phe Val Asp
150             155             160 ttg tca ggt tgg gat aca acc gag ccg aag agt ctt gat gaa tca atc     883
Leu Ser Gly Trp Asp Thr Thr Glu Pro Lys Ser Leu Asp Glu Ser Ile
165             170             175             180 agt gaa gct ttt gct gat atc gat gta tca aaa gaa cta cct atc gtg     931
Ser Glu Ala Phe Ala Asp Ile Asp Val Ser Lys Glu Leu Pro Ile Val
            185             190             195 acg ggt tat gca tat tgt aaa gaa ggt ctt atg cat acg tat gac cga     979
Thr Gly Tyr Ala Tyr Cys Lys Glu Gly Leu Met His Thr Tyr Asp Arg
        200             205             210 ggc tac agt gag atg act ttc agc cga gtt gct tcg atc acg aaa gcg    1027
Gly Tyr Ser Glu Met Thr Phe Ser Arg Val Ala Ser Ile Thr Lys Ala
    215             220             225 aat tta gcg ata atc cac aag gaa tat cac tta agt tct gct gac cca    1075
Asn Leu Ala Ile Ile His Lys Glu Tyr His Leu Ser Ser Ala Asp Pro
230             235             240 cgt gtt gtt ggt cct gag aaa gta ttg cca att ggc agc acg aac tac    1123
Arg Val Val Gly Pro Glu Lys Val Leu Pro Ile Gly Ser Thr Asn Tyr
245             250             255             260 gat gtg gct gac cag ctg gct aac ctg gga atg gaa gct att cac cct    1171
Asp Val Ala Asp Gln Leu Ala Asn Leu Gly Met Glu Ala Ile His Pro
            265             270             275 aac gca gca gcg ggt ttg cgc gaa agt ggt atc gaa ctg cag att aaa    1219
Asn Ala Ala Ala Gly Leu Arg Glu Ser Gly Ile Glu Leu Gln Ile Lys
        280             285             290
```

```
aac aca ttt gaa cct gaa cat gaa ggt act ttg att tct tct ggt tac       1267
Asn Thr Phe Glu Pro Glu His Glu Gly Thr Leu Ile Ser Ser Gly Tyr
        295                 300                 305 cgt cca gag gaa gac aaa gtg gag atc atc gcg ggt aag cag aaa gtg       1315
Arg Pro Glu Glu Asp Lys Val Glu Ile Ile Ala Gly Lys Gln Lys Val
    310                 315                 320 ttt gcg ttg cat ctt ttt gac caa gcg atg gtt ggt aaa gta gat aac       1363
Phe Ala Leu His Leu Phe Asp Gln Ala Met Val Gly Lys Val Asp Asn
325                 330                 335                 340 gtg agt tac gag ctg atg gaa atc atc tca gat gca cac gtg aca ttg       1411
Val Ser Tyr Glu Leu Met Glu Ile Ile Ser Asp Ala His Val Thr Leu
            345                 350                 355 gtt ggt aaa gaa atg aac gcc aac tcg att act tac tac ctg ggc ggt       1459
Val Gly Lys Glu Met Asn Ala Asn Ser Ile Thr Tyr Tyr Leu Gly Gly
        360                 365                 370 aat gca gac agc tta aac aaa gtt ctg tat aaa gcg gaa aaa tgt tac       1507
Asn Ala Asp Ser Leu Asn Lys Val Leu Tyr Lys Ala Glu Lys Cys Tyr
    375                 380                 385 ccg aaa gca tca att aaa ggc cgt atg gta gcg ttg atc tca gcg att       1555
Pro Lys Ala Ser Ile Lys Gly Arg Met Val Ala Leu Ile Ser Ala Ile
390                 395                 400 ggt tct cag att gac acc aac aaa acc ttg gcg aaa ggt gta ttg gca       1603
Gly Ser Gln Ile Asp Thr Asn Lys Thr Leu Ala Lys Gly Val Leu Ala
            405                 410                 415                 420 ctg atg aat agt ggt gtg acg cca gtg gct ctg cac tca tca tta cga       1651
Leu Met Asn Ser Gly Val Thr Pro Val Ala Leu His Ser Ser Leu Arg
        425                 430                 435 aat gtt aat gta caa ttc gtt gtg ggt gat aaa gag tat cag cga gca       1699
Asn Val Asn Val Gln Phe Val Val Gly Asp Lys Glu Tyr Gln Arg Ala
    440                 445                 450 att tgt gca ctg cac gat gag ttc ttc gaa ccg gtt gag aat gct gag       1747
Ile Cys Ala Leu His Asp Glu Phe Phe Glu Pro Val Glu Asn Ala Glu
455                 460                 465 tcg ata gaa gac gtt gcg taagtcaatt acacaacaag acgtgataca              1795
Ser Ile Glu Asp Val Ala
        470 aagggagcct ttctaggctc ctttgttgtt tgtggcttta ctgtgtttat ttcggcaatg     1855 aaaagcggct tatttggacg ataacacacg ggctgtgtgc gtatgcttat ccgttcttta    1915 gcttacactt tctgtcacga caggatttga gtggcgtctg gctatccaat acgcgatacc    1975 gccccagaac acggttagca gccaagggc agtccagtgt ttagccactt gttgccatgt     2035 tgcgcccatt tgatttaagg cgagaaagcc cttaatcgcc caagtactcg ggcttaaatc    2095 agcaacccaa agcaggggag ccggaatgga ttctactggc caaatgaaac cggcaaggaa    2155 gataagtggc attgagctga ccaatacgac taaggtgacc agttctctgc gtggtaaaag    2215 gtaaccgagc caaaaaccca accacagca gctcaacaga acggaaccca gcaaggaaag    2275 cagttcagtt gcctgagcga tgtgattacg ctacctttca aagctggcac caaaat        2331

<210> SEQ ID NO 30
<211> LENGTH: 474
<212> TYPE: PRT
<213> ORGANISM: Vibrio natriegens

<400> SEQUENCE: 30

Met Thr Phe Thr Val Glu Lys Ile Gly Gly Thr Ser Met Thr Ala Phe
1               5                   10                  15

Asp Ala Val Leu Asp Asn Ile Ile Leu Arg Pro Lys Thr Pro Tyr Asn
```

-continued

```
            20                  25                  30
Arg Val Phe Val Val Ser Ala Tyr Gly Gly Met Thr Asp Ala Leu Leu
            35                  40                  45
Glu Cys Lys Lys Thr Ser Lys Ala Gly Val Tyr Gln Leu Val Ala Lys
            50                  55                  60
Arg Asp Asp Ser Trp Glu Ala Leu Ala Tyr Val Glu Asn Arg Met
 65                  70                  75                  80
Leu Leu Thr Asn Glu Asn Ile Phe Ala Asp Pro Met Asn Arg Met Arg
                85                  90                  95
Ala Asp Lys Phe Ile Arg Ser Arg Ile Ser Glu Ala Lys Asn Cys Ile
            100                 105                 110
Ala Asn Ile Leu Glu Thr Cys Gln Tyr Gly Gln Phe Ser Leu Arg His
            115                 120                 125
Tyr Leu Pro Gln Ile Arg Glu Phe Leu Ser Ser Ile Gly Glu Ala His
            130                 135                 140
Ser Ala Tyr Asn Thr Ala Leu Lys Leu Lys Asn Met Gly Ile Asn Ala
145                 150                 155                 160
Lys Phe Val Asp Leu Ser Gly Trp Asp Thr Thr Glu Pro Lys Ser Leu
            165                 170                 175
Asp Glu Ser Ile Ser Glu Ala Phe Ala Asp Ile Asp Val Ser Lys Glu
            180                 185                 190
Leu Pro Ile Val Thr Gly Tyr Ala Tyr Cys Lys Glu Gly Leu Met His
            195                 200                 205
Thr Tyr Asp Arg Gly Tyr Ser Glu Met Thr Phe Ser Arg Val Ala Ser
            210                 215                 220
Ile Thr Lys Ala Asn Leu Ala Ile Ile His Lys Glu Tyr His Leu Ser
225                 230                 235                 240
Ser Ala Asp Pro Arg Val Val Gly Pro Glu Lys Val Leu Pro Ile Gly
            245                 250                 255
Ser Thr Asn Tyr Asp Val Ala Asp Gln Leu Ala Asn Leu Gly Met Glu
            260                 265                 270
Ala Ile His Pro Asn Ala Ala Gly Leu Arg Glu Ser Gly Ile Glu
            275                 280                 285
Leu Gln Ile Lys Asn Thr Phe Glu Pro Glu His Glu Gly Thr Leu Ile
            290                 295                 300
Ser Ser Gly Tyr Arg Pro Glu Glu Asp Lys Val Glu Ile Ala Gly
305                 310                 315                 320
Lys Gln Lys Val Phe Ala Leu His Leu Phe Asp Gln Ala Met Val Gly
            325                 330                 335
Lys Val Asp Asn Val Ser Tyr Glu Leu Met Glu Ile Ile Ser Asp Ala
            340                 345                 350
His Val Thr Leu Val Gly Lys Glu Met Asn Ala Asn Ser Ile Thr Tyr
            355                 360                 365
Tyr Leu Gly Gly Asn Ala Asp Ser Leu Asn Lys Val Leu Tyr Lys Ala
            370                 375                 380
Glu Lys Cys Tyr Pro Lys Ala Ser Ile Lys Gly Arg Met Val Ala Leu
385                 390                 395                 400
Ile Ser Ala Ile Gly Ser Gln Ile Asp Thr Asn Lys Thr Leu Ala Lys
            405                 410                 415
Gly Val Leu Ala Leu Met Asn Ser Gly Val Thr Pro Val Ala Leu His
            420                 425                 430
Ser Ser Leu Arg Asn Val Asn Val Gln Phe Val Val Gly Asp Lys Glu
            435                 440                 445
```

Tyr Gln Arg Ala Ile Cys Ala Leu His Asp Glu Phe Phe Glu Pro Val
    450                 455                 460

Glu Asn Ala Glu Ser Ile Glu Asp Val Ala
465                 470

```
<210> SEQ ID NO 31
<211> LENGTH: 24
<212> TYPE: DNA
<213> ORGANISM: Artificial sequence
<220> FEATURE:
<223> OTHER INFORMATION: primer

<400> SEQUENCE: 31
tgggaattcg tttaagaagt cgtg                                          24

<210> SEQ ID NO 32
<211> LENGTH: 25
<212> TYPE: DNA
<213> ORGANISM: Artificial sequence
<220> FEATURE:
<223> OTHER INFORMATION: primer

<400> SEQUENCE: 32
aaacccgggt tatttttcaa atagc                                         25

<210> SEQ ID NO 33
<211> LENGTH: 25
<212> TYPE: DNA
<213> ORGANISM: Artificial sequence
<220> FEATURE:
<223> OTHER INFORMATION: primer

<400> SEQUENCE: 33
ggggaattct taagaagata cactg                                         25

<210> SEQ ID NO 34
<211> LENGTH: 25
<212> TYPE: DNA
<213> ORGANISM: Artificial sequence
<220> FEATURE:
<223> OTHER INFORMATION: primer

<400> SEQUENCE: 34
tttcccgggt tataccccta gtttc                                         25

<210> SEQ ID NO 35
<211> LENGTH: 25
<212> TYPE: DNA
<213> ORGANISM: Artificial sequence
<220> FEATURE:
<223> OTHER INFORMATION: primer

<400> SEQUENCE: 35
aaagagctca tctgcacagc aatag                                         25

<210> SEQ ID NO 36
<211> LENGTH: 24
<212> TYPE: DNA
<213> ORGANISM: Artificial sequence
<220> FEATURE:
<223> OTHER INFORMATION: primer

<400> SEQUENCE: 36
aaacccgggt tagaatagcc cagc                                          24
```

```
<210> SEQ ID NO 37
<211> LENGTH: 27
<212> TYPE: DNA
<213> ORGANISM: Artificial sequence
<220> FEATURE:
<223> OTHER INFORMATION: primer

<400> SEQUENCE: 37
tttgaattct ttggtcttgg gaaggtg                                              27

<210> SEQ ID NO 38
<211> LENGTH: 24
<212> TYPE: DNA
<213> ORGANISM: Artificial sequence
<220> FEATURE:
<223> OTHER INFORMATION: primer

<400> SEQUENCE: 38
aaacccgggt caccctatta gggc                                                 24

<210> SEQ ID NO 39
<211> LENGTH: 23
<212> TYPE: DNA
<213> ORGANISM: Artificial sequence
<220> FEATURE:
<223> OTHER INFORMATION: primer

<400> SEQUENCE: 39
ggggaattct aagttaccaa tca                                                  23

<210> SEQ ID NO 40
<211> LENGTH: 24
<212> TYPE: DNA
<213> ORGANISM: Artificial sequence
<220> FEATURE:
<223> OTHER INFORMATION: primer

<400> SEQUENCE: 40
aaacccgggt tacgcaacgt cttc                                                 24
```

METHOD FOR PRODUCTION OF L-AMINO ACID

This application is a continuation under 35 U.S.C. §120 of PCT Patent Application No. PCT/JP2008/051643, filed Feb. 1, 2008, which claims priority under 35 U.S.C. §119 to Japanese Patent Application No. 2007-022910, filed on Feb. 1, 2007, which are incorporated in their entireties by reference. The Sequence Listing in electronic format filed herewith is also hereby incorporated by reference in its entirety (File Name: US-401_Seq_List; File Size: 77 KB; Date Created: Jul. 31, 2009).

BACKGROUND OF THE INVENTION

1. Field of the Invention

The present invention relates to a method for producing an L-amino acid using a *Vibrio* bacterium, and more particularly, to a method for producing an L-amino acid such as L-lysine. L-lysine is industrially useful as an additive in animal feeds, and as a component of health foods, amino acid infusions, and the like.

2. Brief Description of the Related Art

L-amino acids such as L-lysine, L-glutamic acid, L-threonine, L-leucine, L-isoleucine, and L-valine are typically produced by fermentation using a coryneform bacterium belonging to the genus *Brevibacterium* or *Corynebacterium*, a bacterium belonging to the genus *Bacillus, Escherichia, Streptomyces, Pseudomonas, Arthrobacter, Serratia, Enterobacter, Pantotea, Methylobacillus,* or *Vibrio*, or a filamentous bacterium belonging to the genus *Penicillium*.

There are well-known methods for producing a target substance such as an L-amino acid by fermentation using a microorganism, such as by using a wild-type microorganism (wild-type strain), using an auxotrophic strain derived from a wild-type strain, using a metabolic regulation mutant that is derived from a wild-type strain as a drug-resistant mutant, and using a strain having properties of both the auxotrophy and the metabolic regulation mutation.

The productivity of the L-amino acids has been significantly enhanced by improvements in chosen microorganism and production methods. However, to further meet increasing needs, producing L-amino acids at a low cost and high efficiency is required for the development of further methods.

It is a longstanding problem in the direct fermentation of L-amino acids is a decrease in the activity of the chosen microorganism caused by an increase in the osmotic pressure due to the accumulation of the product of interest during the culture, resulting in difficulty in keeping the productivity for a long period of time.

The *Vibrio* bacteria are Gram-negative facultative anaerobic bacteria belonging to the Vibrionanceae family in γ-Propionibacteria, and each of the bacteria moves by one polar flagellum. The *Vibrio* bacteria are present in fresh water and seawater.

For example, the following methods using cultures or bacterial cells of *Vibrio* bacteria, or treated products thereof are known: a method of producing L-tryptophan from indol and serine, or indol, pyruvic acid, and ammonium ion (JP 56-85291 A); a method of producing L-methionine from N-carbamylmethionine (JP 62-275696 A); a method of producing L-serine from β-hydroxyaspartic acid (JP 60-62993 A); a method of producing phenylalanine or a derivative thereof from a precursor of phenylalanine (JP 62-289194 A); and a method of producing thymidine by reacting 2-deoxyribose-1-phosphoric acid or a salt thereof with thymine (JP 1-104190 A).

A method of producing a target substance using a microorganism isolated from nature capable of producing the substance is also known. As such a method using a *Vibrio* bacterium, a bacterium which belongs to the genus *Vibrio* and can produce an eicosapentaenoic acid-containing lipid, and a method of producing eicosapentaenoic acid using the bacterium have been reported (JP 63-216490 A).

However, the ability of a *Vibrio* bacterium to produce a target substance such as an amino acid from sugar or the like by direct fermentation has not been previously reported, and an example of production of a target substance from sugar or the like by direct fermentation has not been reported. In addition, a *Vibrio* bacterium whose metabolism or the like has been modified to produce a target substance, and production of the substance using the bacterium are not known, and it has not been previously reported that the *Vibrio* bacterium is able to be employed to solve the above-mentioned problems.

SUMMARY OF THE INVENTION

An aspect of the present invention is to provide a method of producing an L-amino acid such as L-lysine and L-threonine with high efficiency.

An L-amino acid can be produced at a very high efficiency by culturing a *Vibrio* bacterium, which had not been used before for fermentative production of L-amino acids, in a medium.

An aspect of the present invention is to provide a method for producing an L-amino acid by fermentation, comprising culturing a *Vibrio* bacterium having an L-amino acid-producing ability in a medium; and collecting the L-amino acid from the medium.

Another aspect of the present invention is to provide the method as described above, wherein the *Vibrio* bacterium is cultured under high osmotic pressure.

Another aspect of the present invention is to provide the method as described above, wherein the high osmotic pressure is not less than 925 mOsm.

Another aspect of the present invention is to provide the method as described above, wherein the L-amino acid is selected from the group consisting of L-lysine, L-ornithine, L-arginine, L-histidine, L-citrulline, L-isoleucine, L-alanine, L-valine, L-leucine, L-glycine, L-threonine, L-serine, L-proline, L-phenylalanine, L-tyrosine, L-tryptophan, L-cysteine, L-cystin, L-methionine, L-glutamic acid, L-asparginic acid, L-glutamine, L-asparagine, and combinations thereof.

Another aspect of the present invention is to provide the method as described above, wherein the L-amino acid-producing ability is imparted by imparting resistance to an L-amino acid analogue.

Another aspect of the present invention is to provide the method as described above, wherein the bacterium has an enhanced activity of an L-amino acid biosynthesis enzyme.

Another aspect of the present invention is to provide the method as described above, wherein the L-amino acid is L-lysine; and the L-amino acid analogue is selected from the group consisting of S-(2-aminoethyl)-L-cystein (AEC), oxalysine, lysine hydroxamate, γ-methyl lysine, α-chlorocaprolactam, DL-α-amino-ε-caprolactam, α-amino-lauryllactam, asparginic acid analogue, a sulfa drug, quinoid, N-lauroyl leucine, and combinations thereof.

Another aspect of the present invention is to provide the method as described above, wherein the L-amino acid is L-lysine; and the L-amino acid biosynthesis enzyme is selected from the group consisting of dihydropicolate synthase, aspartokinase, aspartate-semialdehyde dehydrogenase, dihydropicolinate reductase, diaminopimelate decarboxylase, and combinations thereof.

Another aspect of the present invention is to provide the method as described above, wherein the dihydropicolate synthase and the aspartokinase are modified to be resistant to feedback inhibition by L-lysine.

Another aspect of the present invention is to provide the method as described above, wherein the bacterium is further modified so that the L-lysine export activity is enhanced.

Another aspect of the present invention is to provide the method as described above, wherein the L-amino acid is L-threonine; and the L-amino acid analogue is α-amino-β-hydroxyvaleric acid.

Another aspect of the present invention is to provide the method as described above, wherein the L-amino acid is L-threonine; and the L-amino acid biosynthesis enzyme is selected from the group consisting of aspartokinase, homoserine dehydrogenase, homoserine kinase, threonine synthase, and combinations thereof.

Another aspect of the present invention is to provide the method as described above, wherein the *Vibrio* bacterium is selected from the group consisting of *Vibrio abalonicus, Vibrio adaptatus, Vibrio aerogenes, Vibrio aestuarianus, Vibrio alginolyticus, Vibrio algosus, Vibrio anguillarum, Vibrio calviensis, Vibrio campbellii, Vibrio carchariae, Vibrio coralliilyticus, Vibrio costicola, Vibrio cyclitrophicus, Vibrio cyclosites, Vibrio diazotrophicus, Vibrio fischeri, Vibrio gazogenes, Vibrio halioticoli, Vibrio harveyi, Vibrio hispanica, Vibrio ichthyoenteri, Vibrio iliopisacarius, Vibrio lentus, Vibrio liquefaciens, Vibrio logei, Vibrio marinagilis, Vibrio marinofulvus, Vibrio marinovulgaris, Vibrio mediterranei, Vibrio metschnikovii, Vibrio mytili, Vibrio natriegens, Vibrio navarrensis, Vibrio nereis, Vibrio nigripulchritudo, Vibrio ordalii, Vibrio oreintalis, Vibrio pectenicida, Vibrio pelagius, Vibrio penaeicida, Vibrio ponticus, Vibrio proteolyticus, Vibrio psychroerythrus, Vibrio salmonicida, Vibrio shiloii, Vibrio splendidus, Vibrio tyrosinaticus, Vibrio viscosus, Vibrio wondanis, Beneckea pelagia*, and *Listonella anguillarum*.

Another aspect of the present invention is to provide an isolated DNA selected from the group consisting of:

(a) a DNA comprising nucleotides 568 to 1,710 of SEQ ID NO: 21;

(b) a DNA that hybridizes with a complementary strand of nucleotides 568 to 1,710 of SEQ ID NO: 21, or a probe prepared from said DNA, under stringent conditions, and encodes a protein having aspartokinase activity;

(c) a DNA comprising nucleotides 633 to 2,942 of SEQ ID NO: 23;

(d) a DNA that hybridizes with a complementary strand of nucleotides 633 to 2,942 of SEQ ID NO: 23, or a probe prepared from said DNA, under stringent conditions, and encoding a protein having aspartokinase activity;

(e) a DNA comprising nucleotides 490 to 2,781 of SEQ ID NO: 25;

(f) a DNA that hybridizes with a complementary strand of nucleotides 490 to 2,781 of SEQ ID NO: 25, or a probe prepared from said DNA, under stringent conditions, and encoding a protein having aspartokinase activity;

(g) a DNA comprising nucleotides 1,117 to 2,409 of SEQ ID NO: 27;

(h) a DNA that hybridizes with a complementary strand of nucleotides 1,117 to 2,409 of SEQ ID NO: 27, or a probe prepared from said DNA, under stringent conditions, and encoding a protein having aspartokinase activity;

(i) a DNA comprising nucleotides 470 to 1,765 of SEQ ID NO: 29; and (j) a DNA that hybridizes with a complementary strand of nucleotides 470 to 1,765 of SEQ ID NO: 29, or a probe prepared from said DNA, under stringent conditions, and encoding a protein having aspartokinase activity.

DETAILED DESCRIPTION OF EXEMPLARY EMBODIMENTS

<1> Bacterium

Figure 1:
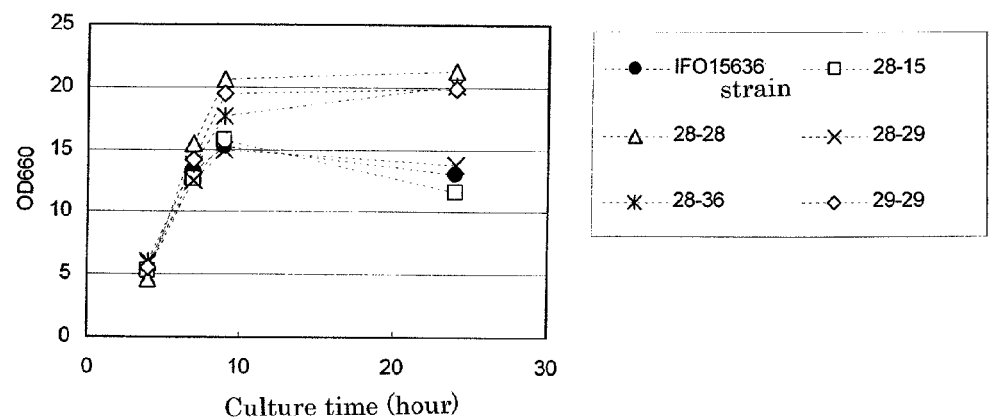
FIG. 1 is a graph showing changes in OD over time of a *V. natriegens* wild-type strain and AEC-resistant strains.

An exemplary bacterium of the present invention (hereinafter, also referred to as "bacterium") is a *Vibrio* bacterium having an L-amino acid-producing ability.

Herein, the phase "L-amino acid-producing ability" refers to an ability to produce and accumulate an L-amino acid at a level that is high enough to be collected from a medium or the bacterial cells when the bacterium is cultured in the medium. That is, the bacterium is a *Vibrio* bacterium which can produce an L-amino acid by fermentation (also referred to as "direct fermentation") using sugar or the like as a carbon source. Therefore, production of an L-amino acid using an exemplary bacterium of the present invention is different from production of an L-amino acid by an enzymatic reaction using bacterial cells as a catalyst.

The *Vibrio* bacterium can have an ability to produce a plurality of L-amino acids. The *Vibrio* bacterium having an L-amino acid-producing ability may originally have an L-amino acid-producing ability, or the ability may be obtained by modifying any one of the *Vibrio* bacteria mentioned below so as to have an L-amino acid-producing ability by using a mutation method or a recombinant DNA technique.

The kind of the L-amino acid is not particularly limited, and examples include basic amino acids such as L-lysine, L-ornithine, L-arginine, L-histidine, and L-citrulline; aliphatic amino acids such as L-isoleucine, L-alanine, L-valine, L-leucine, and L-glycine; hydroxy monoaminocarboxylic acids such as L-threonine and L-serine; cyclic amino acids such as L-proline; aromatic amino acids such as L-phenylalanine, L-tyrosine, and L-tryptophan; sulfur-containing amino acids such as L-cysteine, L-cystine, and L-methionine; and acidic amino acids such as L-glutamic acid, L-aspartic acid, L-glutamine, and L-asparagine. L-lysine is one example. The exemplary bacterium of the present invention may be able to produce two or more kinds of amino acids.

The *Vibrio* bacteria are Gram-negative facultative anaerobic bacteria belonging to Vibrionanceae family of γ-Propionibacteria, and each of the bacteria moves by one polar flagellum and is present in fresh water and seawater. The *Vibrio* bacterium can be nonpathogenic. Such nonpathogenic *Vibrio* bacteria are listed in Biosafety level 1 (Biosafety in Microbiological and Biomedical Laboratories (BMBL) 4th Edition published by Office of Health and Safety (OHS)), and the following *Vibrio* bacteria may be used.

*Vibrio abalonicus* ATCC27390
*Vibrio adaptatus* ATCC19263
*Vibrio aerogenes* ATCC700797
*Vibrio aestuarianus* ATCC35048
*Vibrio alginolyticus* ATCC14582
*Vibrio algosus* ATCC14390
*Vibrio anguillarum* ATCC43305
*Vibrio calviensis* ATCC BAA-606
*Vibrio campbellii* ATCC25920
*Vibrio carchariae* ATCC35084
*Vibrio coralliilyticus* ATCC BAA-450
*Vibrio costicola* ATCC43147
*Vibrio cyclitrophicus* ATCC700982
*Vibrio cyclosites* ATCC14635
*Vibrio diazotrophicus* ATCC33466
*Vibrio fischeri* ATCC25918
*Vibrio gazogenes* ATCC29988
*Vibrio halioticoli* ATCC700680
*Vibrio harveyi* ATCC14126
*Vibrio hispanica* ATCC51589
*Vibrio ichthyoenteri* ATCC700023
*Vibrio iliopiscarius* ATCC51760
*Vibrio lentus* ATCC BAA-539
*Vibrio liquefaciens* ATCC17058
*Vibrio logei* ATCC15382
*Vibrio marinagilis* ATCC14398
*Vibrio marinofulvus* ATCC14395
*Vibrio marinovulgaris* ATCC14394
*Vibrio mediterranei* ATCC43341
*Vibrio metschnikovii* ATCC7708
*Vibrio mytili* ATCC51288
*Vibrio natriegens* ATCC14048
*Vibrio navarrensis* ATCC51183
*Vibrio nereis* ATCC25917
*Vibrio nigripulchritudo* ATCC27043
*Vibrio ordalii* ATCC33509
*Vibrio orientalis* ATCC33933
*Vibrio pectenicida* ATCC700783
*Vibrio pelagius* ATCC33504
*Vibrio penaeicida* ATCC51841
*Vibrio ponticus* ATCC14391
*Vibrio proteolyticus* ATCC53559
*Vibrio psychroerythrus* ATCC27364
*Vibrio salmonicida* ATCC43839
*Vibrio shiloii* ATCC BAA-91
*Vibrio splendidus* ATCC33125
*Vibrio tyrosinaticus* ATCC19378
*Vibrio viscosus* ATCC BAA-105
*Vibrio wodanis* ATCC BAA-104
*Beneckea pelagia* ATCC25916
*Listonella anguillarum* ATCC19264

*Beneckea pelagia* and *Listonella anguillarum* are closely related to the *Vibrio* bacteria, and according to the current classification, are sometimes classified as *Vibrio* bacteria (Thompson, F. L. et al. (2004) Microbiol. Mol. Biol. Rev., 23, 403-431 and Macian, M. C. et al. (2000) Syst. Appl. Microbiol., 23, 373-375). Therefore, these bacteria are also exemplary *Vibrio* bacteria of the present invention.

Of these, *Vibrio natriegens* is one example. *Vibrio natriegens* is a marine-derived facultative anaerobic bacterium belonging to Vibrionanceae family of γ-Propionibacteria and classified as an uronic acid-oxidizing bacterium in 1958 (Payne, W. J. (1958) J. Bacteriology, 76, 301). At first, the bacterium was considered to belong to *Psuedomonas* of γ-Propionibacteria, but the bacterium was re-classified into the genus *Beneckea* and then incorporated into the genus *Vibrio* along with other bacteria belonging to the genus *Beneckea*. The bacterium is classified as Biosafety level 1 in ATCC and classified as Risk Group 1 (German classification) in the German National Resource Centre for Biological Material (DSMZ), and the bacterium is considered to be nonpathogenic.

As *Vibrio natriegens*, *Vibrio natriegens* IFO15636 strain (ATCC14048) strain may be used.

The above-mentioned *Vibrio* bacteria may be obtained from, for example, the American Type Culture Collection (address: P.O. Box 1549, Manassas, Va. 20108, United States of America). That is, accession numbers are given to the strains, and the strains can be obtained using the numbers (refer to www.atcc.org/). The accession numbers corresponding to the respective strains are described in the catalogue of the American Type Culture Collection.

The *Vibrio* bacterium grows well as compared with microorganisms which have been used for production of an L-amino acid (such as *Escherichia coli* and coryneform bacteria), even under high osmotic pressure at a later stage of amino acid fermentation when the produced substance is present at a high level, or when the osmotic pressure is high due to a high sugar concentration. The "high osmotic pressure" includes, for example, not less than 925 mOsm, or as another example, not less than 1,100 mOsm, and as another example, not less than 1,500 mOsm. The upper limit of the osmotic pressure is not particularly limited as long as the amino acid fermentation can be performed, and is, for example, 2,000 mOsm. In addition, the phrase "can grow well under high osmotic pressure" means that the growth rate decreases only to about 90% of the maximum growth rate at 1,100 mOsm when the growth rate of an *E. coli* wild-type strain decreases to 50% or less of the maximum growth rate.

<2> Method of Imparting L-Amino Acid-Producing Ability to a *Vibrio* Bacterium

L-amino acid-producing *Vibrio* bacteria can be obtained by imparting L-amino acid-producing ability to a wild-type strain of *Vibrio* bacterium as described above. In order to impart the L-amino acid-producing ability, methods can be used which are typically used in the conventional breeding of coryneform bacteria, *Escherichia* bacteria or the like, such as by acquiring nutrient-auxotrophic mutant strains, analogue resistant strains, or metabolic regulation mutant strains, or by creating recombinant strains having enhanced expression of L-amino acid biosynthetic enzymes (Amino Acid Fermentation, Japan Scientific Societies Press, first edition publication: May 30, 1986, p. 77 to 100). Activities of L-amino acid biosynthetic enzymes can be enhanced by increasing the copy number of a gene encoding each enzyme or modifying an expression regulatory sequence of the gene. In breeding an L-amino acid-producing bacterium, imparting of such properties such as nutrient-auxotrophy, analogue-resistance and metabolic regulation mutation can be combined with enhancing the expression of the L-amino acid biosynthetic enzymes. Methods of imparting L-amino acid-producing ability are exemplified below.

L-Lysine Producing Bacterium

L-lysine-producing bacteria can be bred to be mutant strains that are auxotrophic for L-homoserine, or L-threonine and L-methionine (JP48-28078B and JP56-6499B), mutant strains that are auxotrophic for inositol or acetate (JP55-9784A and JP56-8692A) or mutant strains that are resistant to oxalysine, lysine hydroxamate, S-(2-aminoethyl)-L-cysteine (AEC), γ-methyllysine, α-chlorocaprolactam, DL-α-amino-ε-caprolactam, α-amino-lauryllactam, aspartate analogs, sulfa drugs, quinoids, and N-lauroylleucine. It is one example to breed a strain that is resistant to S-(2-aminoethyl)-L-cysteine (AEC) as an L-lysine analog.

Methods for mutagenesis to obtain a mutant strain of a *Vibrio* bacterium include ultraviolet irradiation, and treatment with a conventional mutagen such as N-methyl-N'-nitro-N-nitrosoguanidine (NTG) and nitrous acid. L-amino acid-producing *Vibrio* bacterium can also be obtained by selecting naturally occurring mutants of a *Vibrio* bacterium.

For example, L-amino acid analog-resistant mutants can be obtained by inoculating mutated *Vibrio* bacteria on an agar medium containing several concentrations of the L-amino acid analog and selecting a strain that forms a colony.

Nutrient-auxotrophic mutants can be obtained by allowing *Vibrio* bacteria to form a colony on agar-medium containing a specific nutrient such as an L-amino acid and then replicating the colony on another agar medium not containing the nutrient and selecting a strain that cannot form a colony on the medium not containing the nutrient. An example of a L-lysine producing strain of *Vibrio* bacterium includes *Vibrio natriegens* AJ110593 (FERM BP-10946). This strain was deposited at the National Institute of Advanced Industrial Science and Technology, International Patent Organism Depositary (Tsukuba Central 6, 1-1, Higashi 1-Chome, Tsukuba-shi, Ibaraki-ken, 305-8566, Japan) on Oct. 24, 2006 and received an accession number of FERM P-21066. Then, it was converted to an international deposit under the Budapest Treaty, and received an accession number of FERM BP-10946.

Next, methods for imparting or enhancing L-lysine producing ability by enhancing activities of L-lysine biosynthetic enzymes are exemplified.

For example, L-lysine producing ability can be imparted by enhancing dihydrodipicolinate synthase activity and/or aspartokinase activity.

Enhancement of dihydrodipicolinate synthase activity and/or aspartokinase activity of a *Vibrio* bacterium can be performed by constructing a recombinant DNA in which gene fragments encoding dihydrodipicolinate synthase and/or aspartokinase are ligated to a vector, preferably a multi-copy vector that functions in *Vibrio* bacteria and introducing the DNA into a host *Vibrio* bacterium for transformation. Activities of these enzymes are enhanced as a result of increase in copy number of genes encoding dihydrodipicolinate synthase and/or aspartokinase in the cells of the transformed strain. Hereinafter, dihydrodipicolinate synthase may be abbreviated as DDPS, and aspartokinase may be abbreviated as AK, and aspartokinase III may be abbreviated as AK III.

Any microorganism may be a donor of the gene encoding DDPS and the gene encoding AK as long as the genes express DDPS activity and AK activity in *Vibrio* bacteria. The microorganism may be a wild-type or a mutant that is derived from a wild-type strain. Specific examples thereof include *E. coli* (*Escherichia coli*) K-12 strain and *Vibrio natriegens* IFO15636 strain. Nucleotide sequences of a gene encoding DDPS from *Escherichia* bacterium (dapA, Richaud, F. et al. J. Bacteriol., 297 (1986)) and a gene encoding AKIII from *Escherichia* bacterium (lysC, Cassan, M., Parsot, C., Cohen, G. N. and Patte, J. C., J. Biol. Chem., 261, 1052 (1986)) are known. So, these genes can be obtained by synthesizing primers based on the nucleotide sequences and performing PCR using a chromosomal DNA of bacteria such as *E. coli* K-12 strain or *Vibrio natriegens* IFO15636 strain as a template.

Genes from *Vibrio* bacteria can also be obtained from the GenBank database information as shown below.

*Vibrio cholerae* O1 *biovar eltor* str. N16961 chromosome I, complete sequence; AE003852

*Vibrio cholerae* O1 *biovar eltor* str. N16961 chromosome II, complete sequence; AE003853

*Vibrio parahaemolyticus* RIMD 2210633 chromosome I, complete sequence; BA000031

*Vibrio parahaemolyticus* RIMD 2210633 chromosome II, complete sequence; BA000032

*Vibrio fischeri* ES114 chromosome I, complete sequence; CP000020

*Vibrio fischeri* ES114 chromosome II, complete sequence; CP000021

*Vibrio vulnificus* CMCP6 chromosome I, complete sequence; AE016795

*Vibrio vulnificus* CMCP6 chromosome II, complete sequence; AE016796

*Vibrio vulnificus* YJ016 chromosome I, complete sequence; BA000037

*Vibrio vulnificus* YJ016 chromosome II, complete sequence; BA000038

DDPS and AK are preferably not subject to feedback inhibition by L-lysine. It is known that wild-type DDPS derived from *Vibrio* bacterium is regulated by feedback inhibition by L-lysine, and wild-type AKIII derived from *Vibrio* bacterium is regulated by feedback inhibition by L-lysine. Therefore, the dapA and lysC which are introduced into a *Vibrio* bacterium encode DDPS and AK which have a mutation that eliminates the feedback inhibition by L-lysine, respectively. However, DDPS and AK are not necessarily mutant types. For example, DDPS from bacteria belonging to *Corynebacterium* is originally resistant to feedback inhibition by L-lysine.

Homologues of the gene encoding aspartokinase are known, and any gene from any source can be used as long as it encodes a protein having aspartokinase activity. For example, AK genes from *Vibrio natriegens* include the AKO gene, thrA gene, metL gene, lysC gene, and a putative-AK gene.

SEQ ID NO: 21 shows the nucleotide sequence of the region including AKO gene from *Vibrio natriegens*. In SEQ ID NO: 21, it is predicted that the translation initiation codon is GTG at nucleotides 526-528, GTG at nucleotides at 544-546, or GTG at nucleotides 568-570, and the stop codon is TGA at nucleotides at 1711-1713. Therefore, DNA having the open reading frame of nucleotides 526-1710 of SEQ ID NO: 21 (encoding amino acids 1-395 of SEQ ID NO: 22), nucleotides 544-1710 of SEQ ID NO: 21 (encoding amino acids 7-395 of SEQ ID NO: 22), or nucleotides 568-1710 of SEQ ID NO: 21 (encoding amino acids 15-395 of SEQ ID NO: 22) can be used as AKO gene.

SEQ ID NO: 23 shows the nucleotide sequence of the region including thrA gene from *Vibrio natriegens*. In SEQ ID NO: 23, it is predicted that the translation initiation codon is ATG at nucleotides 486-488, GTG at nucleotides at 591-593, or GTG at nucleotides 633-635, and the stop codon is TAA at nucleotides at 2943-2945. Therefore, DNA having the open reading frame of nucleotides 486-2942 of SEQ ID NO: 23 (encoding amino acids 1-819 of SEQ ID NO: 24), nucleotides 591-2942 of SEQ ID NO: 23 (encoding amino acids 35-819 of SEQ ID NO: 24), or nucleotides 633-2942 of SEQ ID NO: 23 (encoding amino acids 50-819 of SEQ ID NO: 24) can be used as thrA gene.

SEQ ID NO: 25 shows the nucleotide sequence of the region including metL gene from *Vibrio natriegens*. In SEQ ID NO: 25, it is predicted that the translation initiation codon is ATG at nucleotides 376-378, GTG at nucleotides at 487-

489, or GTG at nucleotides 490-492, and the stop codon is TAA at nucleotides at 2782-2784. Therefore, DNA having the open reading frame of nucleotides 376-2781 of SEQ ID NO: 25 (encoding amino acids 1-802 of SEQ ID NO: 26), nucleotides 487-2781 of SEQ ID NO: 25 (encoding amino acids 38-802 of SEQ ID NO: 26), or nucleotides 490-2781 of SEQ ID NO: 25 (encoding amino acids 39-802 of SEQ ID NO: 26) can be used as metL gene.

SEQ ID NO: 27 shows the nucleotide sequence of the region including lysC gene from *Vibrio natriegens*. In SEQ ID NO: 27, it is predicted that the translation initiation codon is GTG at nucleotides 1060-1062, or ATG at nucleotides 1117-1119, and the stop codon is TAA at nucleotides at 2410-2412. Therefore, DNA having the open reading frame of nucleotides 1060-2409 of SEQ ID NO: 27 (encoding amino acids 1-450 of SEQ ID NO: 28), or nucleotides 1117-2409 of SEQ ID NO: 27 (encoding amino acids 20-450 of SEQ ID NO: 28) can be used as lysC gene.

SEQ ID NO: 29 shows the nucleotide sequence of the region including the putative-AK gene from *Vibrio natriegens*. In SEQ ID NO: 23, it is predicted that the translation initiation codon is ATG at nucleotides 344-346, ATG at nucleotides at 380-382, or ATG at nucleotides 470-472, and the stop codon is TAA at nucleotides at 1766-1768. Therefore, DNA having the open reading frame of nucleotides 344-1765 of SEQ ID NO: 29 (encoding amino acids 1-474 of SEQ ID NO: 30), nucleotides 380-1765 of SEQ ID NO: 29 (encoding amino acids 13-474 of SEQ ID NO: 30), or nucleotides 470-1765 of SEQ ID NO: 29 (encoding amino acids 43-474 of SEQ ID NO: 30) can be used as putative-AK gene.

The above-described AKO gene, thrA gene, metL gene, lysC gene and the putative AK gene may hybridize with a complementary strand of each of the sequences, or a probe prepared from these sequences, under stringent conditions and encodes a protein having aspartokinase activity.

The term "stringent conditions" refers to conditions where a so-called specific hybrid is formed and a non-specific hybrid is not formed. It is difficult to clearly define the conditions by numerical value, but examples thereof include conditions where DNAs having high identity, for example, at least 80%, preferably 90%, more preferably 95%, and further more preferably 97% identity hybridize with each other and DNAs having homology less than the value do not hybridize with each other; and specifically include washing conditions typical of Southern hybridization, e.g., washing at 60° C., 1×SSC, 0.1% SDS, preferably 0.1×SSC, 0.1% SDS, more preferably 68° C., 0.1×SSC, 0.1% SDS, once or preferably twice or three times.

Aspartokinase activity can be measured according to the method described in Miyajima, R et al (The Journal of Biochemistry (1968), 63(2), 139-148).

The above-described AKO gene, thrA gene, metL gene, lysC gene and putative AK gene are not limited to wild-type genes and may be mutant or artificially modified genes that encode a protein having the amino acid sequence encoded by each of the open reading frames, but which include substitutions, deletions, insertions, and/or additions of one or several amino acids at one or a plurality of positions, as long as the genes encode a protein having aspartokinase activity.

In the present invention, the term "one or several" specifically means 1 to 20, or in another example, 1 to 10, or in another example, 1 to 5, although this determination depends on the position in the protein's tertiary structure or the types of amino acid residues in the protein. The above-mentioned substitution is preferably a conservative substitution, which may include substitutions between aromatic amino acids such as substitution among Phe, Trp and Tyr, substitution between hydrophobic amino acids such as substitution among Leu, Ile and Val, substitution between polar amino acids such as substitution between Gln and Asn, substitution between basic amino acids such as substitution among Lys, Arg and His, substitution between acidic amino acids such as substitution between Asp and Glu, substitution between hydroxyl group-containing amino acids such as substitution between Ser and Thr. Examples of conservative substitutions include substitution of Ser or Thr for Ala; substitution of Gln, His or Lys for Arg; substitution of Glu, Gln, Lys, His or Asp for Asn; substitution of Asn, Glu or Gln for Asp; substitution of Ser or Ala for Cys; substitution of Asn, Glu, Lys, His, Asp or Arg for Gln; substitution of Gly, Asn, Gln, Lys or Asp for Glu; substitution of Pro for Gly; substitution of Asn, Lys, Gln, Arg or Tyr for His; substitution of Leu, Met, Val or Phe for Ile; substitution of Ile, Met, Val or Phe for Leu; substitution of Asn, Glu, Gln, His or Arg for Lys; substitution of Ile, Leu, Val or Phe for Met; substitution of Trp, Tyr, Met, Ile or Leu for Phe; substitution of Thr or Ala for Ser; substitution of Ser or Ala for Thr; substitution of Phe or Tyr for Trp; substitution of His, Phe or Trp for Tyr; and substitution of Met, Ile or Leu for Val. Meanwhile, the above-mentioned amino acid substitution, deletion, insertion, addition or inversion may be a result of a naturally-occurring mutation (mutant or variant) due to an individual difference, a difference of species of a bacterium harboring the AKO gene, thrA gene, metL gene, lysC gene or putative AK. Such a homologue gene can be obtained by modifying the nucleotide sequence of each of the above-described open reading frames with site-specific mutagenesis so that the modified gene encodes a protein that has a substitution, deletion, insertion or addition of the amino acid residue at a specific position.

The AKO gene, thrA gene, metL gene, lysC gene and putative AK include genes that encode amino acid sequences having identity of not less than 80%, preferably not less than 90%, more preferably not less than 95%, particularly preferably not less than 97% to the entire amino acid sequences encoded by the above-described open reading frame and encode a protein which has aspartokinase activity. The identity of amino acid sequences and nucleotide sequences may be determined by using, for example, an algorithm BLAST (Proc. Natl. Acad. Sci. USA, 90, 5873 (1993)) or FASTA (Methods Enzymol., 183, 63 (1990)) created by Karlin and Altschul. Based on the algorithm BLAST, programs called BLASTN and BLASTX have been developed (www.ncbi.nlm.nih.gov).

Plasmids to be used for gene cloning are those replicable in bacteria such as *Escherichia* bacteria and specific examples thereof include pBR322, pTWV228, pMW119 and pUC19.

Vectors that function in *Vibrio* bacteria include any vectors that are autonomously replicable in *Vibrio* bacteria. Vector plasmids include those having an ori that is derived from the pUC plasmid, pACYC184 plasmid, or IncQ plasmid. Markers include kanamycin-resistant gene derived from Tn903, chloramphenicol resistant gene derived from Tn9, streptomycin resistant gene, and a tetracycline resistant gene.

In order to prepare a recombinant DNA by ligating dapA and lysC to a vector that functions in *Vibrio* bacteria, the vector is digested with restriction enzymes that correspond to the terminal of DNA fragments containing dapA and lysC. Ligation can be usually performed by using a ligase such as T4 DNA ligase. dapA and lysC may be carried by separate vectors or by a single vector.

An example of a DNA encoding mutant dihydrodipicolinate synthase desensitized to feedback inhibition by L-lysine includes a DNA encoding a protein which has an amino acid sequence in which the histidine at position 118 is replaced by tyrosine. Meanwhile, an example of a DNA encoding mutant aspartokinase desensitized to feedback inhibition by L-lysine includes a DNA encoding an AKIII having an amino acid sequence in which the threonine at position 352, the glycine at position 323, and the methionine at position 318 are replaced by isoleucine, asparagine and isoleucine, respectively (U.S. Pat. No. 5,661,012 and U.S. Pat. No. 6,040,160). Such mutant DNAs can be obtained by a site-specific mutation using PCR or the like.

Wide host-range plasmids RSFD80, pCAB1, and pCABD2 are known to contain a mutant dapA gene encoding a mutant dihydrodipicolinate synthase and a mutant lysC gene encoding a mutant aspartokinase (U.S. Pat. No. 6,040, 160). *Escherichia coli* JM109 strain transformed with RSFD80 was named AJ12396 (U.S. Pat. No. 6,040,160), and the strain was deposited at the National Institute of Bioscience and Human-Technology, Agency of Industrial Science and Technology, Ministry of International Trade and Industry (currently, International Patent Organism Depositary, National Institute of Advanced Industrial Science and Technology; Tsukuba Central 6, 1-1, Higashi 1-Chome, Tsukuba-shi, Ibaraki-ken, 305-8566, Japan) on Oct. 28, 1993 and given an accession number of FERM P-13936, and the deposit was then converted to an international deposit under the provisions of Budapest Treaty on Nov. 1, 1994 and given an accession number of FERM BP-4859. RSFD80 can be obtained from AJ12396 strain by a conventional method.

The recombinant DNA prepared as described above is introduced into a *Vibrio* bacterium by any method that enables sufficient transformation efficiency and an example thereof includes electroporation (Canadian Journal of Microbiology, 43. 197 (1997)).

DDPS activity and/or AK activity can also be enhanced by introducing multiple copies of the dapA and/or lysC into the chromosomal DNA of a bacterium. Introduction of multiple copies of the genes into the chromosomal DNA of a bacterium can be attained by homologous recombination using a target sequence present on the chromosomal DNA in multiple copies. Such a sequence present on a chromosomal DNA in multiple copies may be a repetitive DNA or an inverted repeat present on the edge of a transposing element. Alternatively, as disclosed in JP 2-109985 A, multiple copies of dapA and/or lysC can be introduced into the chromosomal DNA by inserting the genes into a transposon, and transferring it so that multiple copies of the gene are integrated into the chromosomal DNA. These methods increase the copy number of dapA and/or lysC which leads to enhancement in DDPS activity and/or AK activity.

Besides the above-described gene amplification methods, the enhancement of DDPS activity and/or AK activity can also be performed by replacing an expression regulatory sequence such as a promoter of dapA and/or lysC with a potent sequence (JP1-215280). Examples of potent promoters include the lac promoter, trp promoter, trc promoter, tac promoter, lambda phage PR promoter, PL promoter, tet promoter, amyE promoter, spac promoter. Replacement with these promoters enhance the expression of dapA and/or lysC, thereby DDPS activity and/or AK activity are increased. Replacing an expression regulatory sequence may be combined with increasing the copy number of dapA and/or lysC.

DNA digestion, ligation, preparation of chromosomal DNA, PCR, preparation of plasmid DNA, transformation, design of oligonucleotides to be used as primers can be performed according to conventional methods well-known to skilled artisan. These methods are described in Sambrook, J., Fritsch, E. F., and Maniatis, T., "Molecular Cloning A Laboratory Manual, Second Edition", Cold Spring Harbor Laboratory Press, (1989).

In addition to enhancement of DDPS activity and/or AK activity, activities of other enzymes involved in L-lysine biosynthesis may be enhanced. Examples of such enzymes include enzymes in the diaminopimelate pathway such as dihydrodipicolinate reductase (dapB), diaminopimelate decarboxylase (lysA), diaminopimelate dehydrogenase (ddh) (WO96/40934), phosphoenolpyruvate carboxylase (ppc) (JP 60-87788 A), aspartate aminotransferase (aspC) (JP 06-102028 B), diaminopimelate epimerase (dapF) (JP 2003-135066), and aspartate semialdehyde dehydrogenase (asd) (WO 00/61723); and genes encoding enzymes in the aminoadipic acid pathway such as homoaconitate hydratase (JP 2000-157276 A). The words in parentheses represent the gene names (same is true in the following descriptions).

The *Vibrio* bacterium may have enhanced L-lysine producing ability due to enhancement of L-lysine-export activity. For example, L-lysine-export ability can be enhanced by increasing the expression of the ybjE gene or lysE gene (JP2005-237379, WO97/23697).

Furthermore, in the bacterium, an activity of an enzyme that catalyzes a reaction which branches off from L-amino acid biosynthetic pathway and produces other compound may be decreased or may be made deficient. Examples of such an enzyme for L-lysine production include homoserine dehydrogenase, lysine decarboxylase (cadA, ldcC), and malic enzyme, and strains in which activities of such enzymes are decreased or deficient are described in WO 95/23864, WO 96/17930, WO 2005/010175, and the like.

Activities of these enzymes can be decreased or eliminated by introducing a mutation to the genes encoding the enzymes on the chromosome using a known mutation treatment, to thereby decrease or eliminate the activities of the enzymes in a cell. For example, decreasing or eliminating the activities of the enzymes can be attained by disrupting the genes encoding the enzymes on the chromosome by gene recombination or by modifying an expression regulatory sequence such as a promoter or Shine-Dalgarno (SD) sequence. In addition, this can also be attained by introducing an amino acid substitution (missense mutation) to the region encoding the enzymes on the chromosome, introducing a stop codon (nonsense mutation), introducing a frameshift mutation that adds or deletes one or two nucleotides, or deleting part of the gene (Journal of Biological Chemistry 272: 8611-8617 (1997). Meanwhile, the activities of the enzymes can also be decreased or eliminated by constructing a mutant gene encoding a mutant enzyme which has a deletion in the coding region, and then replacing the normal gene on the chromosome with the mutant gene by homologous recombination, or introducing the mutant gene using a transposon or an IS factor.

For example, the following gene recombination method can be used to introduce a mutation that decreases or eliminates the activities of the above-mentioned enzymes. A mutant gene is prepared by modifying a partial sequence of a target gene so that it does not encode an enzyme that can function normally. Then, a *Vibrio* bacterium is transformed with a DNA containing the mutant gene to cause recombination of a gene on the bacterial chromosome with the mutant gene, thereby substituting the target gene on the chromosome with the mutant gene. Examples of this type of gene substitution using homologous recombination include the method using a linear DNA called "Red-driven integration" (Datsenko, K. A, and Wanner, B. L. Proc. Natl. Acad. Sci. USA. 97: 6640-6645 (2000), a combination of Red-driven integration and a cleavage system derived from λ phage (Cho, E. H., Gumport, R. I., Gardner, J. F. J. Bacteriol. 184: 5200-5203 (2002)) (WO 2005/010175), a method using a plasmid containing a temperature-sensitive replication origin (Datsenko, K. A, and Wanner, B. L. Proc. Natl. Acad. Sci. USA. 97: 6640-6645 (2000); U.S. Pat. No. 6,303,383; JP 05-007491 A), and the like. Meanwhile, a site-specific mutation by gene substitution using homologous recombination can also be performed by using a plasmid which is not able to replicate in a host cell.

The above-described methods of enhancing or decreasing activities of enzymes involved in L-lysine biosynthesis can be applied to breeding bacteria that produce other L-amino acids. Hereinafter, methods of breeding bacteria that produce other L-amino acids will be described.

L-tryptophan-producing bacteria can be constructed by enhancing one or more activities of the enzymes selected from anthranilate synthase, phosphoglycerate dehydrogenase, and tryptophan synthase. The anthranilate synthase and phosphoglycerate dehydrogenase are both subject to feedback inhibition by L-tryptophan and L-serine, so a mutation which results in resistance to the feedback inhibition can be introduced into these enzymes. Specifically, a *Vibrio* bacterium harboring the feedback-resistant enzymes can be obtained by mutating the anthranilate synthase and phosphoglycerate dehydrogenase so as to be resistant to the feedback inhibition and introducing the mutant enzymes into the bacterium (WO94/08031).

A strain introduced with a recombinant DNA comprising the tryptophan operon is also a preferable L-tryptophan-producing bacterium. Specifically, a tryptophan operon which contains a gene encoding desensitized anthranilate synthase can be introduced (JP 57-71397 A, JP 62-244382 A, U.S. Pat. No. 4,371,614). Moreover, L-tryptophan-producing ability can be enhanced or imparted by enhancing expression of a gene which encodes tryptophan synthase, among tryptophan operons (trpBA). The tryptophan synthase consists of α and β subunits which are encoded by trpA and trpB, respectively.

An L-tryptophan-producing bacterium is also preferably obtained by making deficient a trpR (a repressor of tryptophan operon) or by introducing a mutation in trpR (U.S. Pat. No. 4,371,614 and WO2005/056776).

An L-tryptophan-producing bacterium can also be constructed by a modification which imparts auxotrophy for L-phenylalanine and L-tyrosine.

An L-tryptophan-producing bacterium can also be constructed by enhancing 3-phosphoserine phosphatase (serB) activity (U.S. Pat. No. 4,371,614) or phosphoenolpyruvate carboxykinase (pckA) activity.

L-tryptophan, L-phenylalanine and L-tyrosine are aromatic amino acids and have a common synthetic pathway. Examples of aromatic amino acid synthetic enzymes include 3-deoxyarabino-heptulosonic acid 7-phosphate synthase (aroG), 3-dehydrokinate synthase (aroB), shikimic acid dehydratase, shikimic acid kinase (aroL), 5-enol-pyruvylshikimic acid 3-phosphate synthase (aroA), and chorismic acid synthase (aroC) (EP763127A). Thus, the ability to produce these aromatic amino acids can be enhanced by increasing the copy number of a gene encoding one or more of these enzymes with a plasmid or on a chromosome. Furthermore, these genes are regulated by tyrosine repressor (tyrR) and therefore the ability to produce these aromatic amino acids can be enhanced by disrupting the tyrR gene (EP763127A).

Furthermore, if the ability to produce one of the amino acid is to be enhanced, the biosynthesis pathway of the other amino acid can be attenuated. For example, L-phenylalanine biosynthesis pathway and L-tyrosine biosynthesis pathway can be attenuated in order to produce L-tryptophan as a target amino acid (U.S. Pat. No. 4,371,614).

3-deoxyarabino-heptulosonic acid 7-phosphate synthase (aroF and aroG) is sensitive to feeback inhibition by aromatic amino acids, so the enzyme may be modified so as to be resistant to the feedback inhibition. For example, aromatic amino acids can be efficiently produced by introducing into host a mutant aroF gene which encodes a mutant enzyme in which aspartic acid residue at position 147 and serine residue at position 181 are replaced with another amino acid residue and a mutant aroG gene encoding a mutant enzyme in which one of aspartic acid residue at position 146, methionine residue at position 147, proline residue at position 150, alanine residue at position 202 is replaced with another amino acid residue or both of methionine residue at position 157 and alanine residue at position 219 are replaced with another amino acid residue (EP0488424).

Besides the above-described modifications, a L-phenylalanine producing strain can be deficient in tyrA and tyrR or a phenylalanine-export gene, such as yddG and yedA, can be amplified.

L-threonine-producing *Vibrio* bacteria can be preferably obtained by enhancing activities of L-threonine biosynthetic enzymes. Examples of genes encoding L-threonine synthetic enzymes include aspartokinase III gene (lysC), aspartate semialdehyde dehydrogenase (asd), and aspartokinase I gene (thrA), homoserine kinase gene (thrB), and threonine synthase gene (thrC) which are encoded by threonine operon. Two or more of the genes may be introduced. The genes encoding L-threonine synthetic enzymes can be introduced into a *Vibrio* bacterium in which threonine decomposition is decreased. For example, L-threonine decomposition can be suppressed by decreasing threonine dehydrogenase activity.

Activities of L-threonine biosynthetic enzymes are inhibited by end product L-threonine, so L-threonine biosynthetic enzymes are preferably modified so as to be desensitized to feedback inhibition by L-threonine when constructing L-threonine producing strains. The above-described thrA gene, thrB gene and thrC gene constitute threonine operon whose promoter has an attenuator structure. Since the expression of threonine operon is inhibited by isoleucine and threonine in the culture medium and also inhibited by attenuation, the threonine operon can be modified by removing leader sequence or attenuator in the attenuation region (Lynn, S. P., Burton, W. S., Donohue, T. J., Gould, R. M., Gumport, R. I., and Gardner, J. F. J. Mol. Biol. 194:59-69 (1987); WO02/26993; WO2005/049808).

Furthermore, *Vibrio* bacteria modified to be desensitized to feedback inhibition by L-threonine can be obtained by imparting resistance to α-amino β-hydroxy isovaleric acid (AHV).

The gene encoding aspartokinase (lysC) can be modified to be desensitized to feedback inhibition by L-lysine. Such a lysC gene modified to be desensitized to feedback inhibition can be obtained from the above-described gene.

Besides L-threonine biosynthetic enzymes, L-threonine producing bacterium can also be bred to enhance expression of genes involved in glycolytic pathway, TCA cycle, or respiratory chain, or genes that regulate the expression of these genes, or genes involved in sugar uptake. Examples of these genes that are effective for L-threonine production include transhydrogenase gene (pntAB)(EP733712B), phosphoenolpyruvate carboxylase gene (pepC)(WO95/06114), phosphoenolpyruvate synthase gene (pps)(EP877090B), pyruvate carboxylase gene derived from coryneform bacterium or *Bacillus* bacterium (WO99/18228, EP1092776A).

Expression of a gene that imparts L-threonine resistance and/or a gene that imparts L-homoserine resistance, or both can be enhanced in a host bacterium. Examples of the genes that impart L-threonine resistance include rhtA gene (Res. Microbiol. 154:123-135 (2003)), rhtB gene (EP0994190A), rhtC gene (EP1013765A), yfiK gene and yeaS gene (EP1016710A). Methods for imparting L-threonine resistance to a host bacterium are described in EP0994190A or WO90/04636.

L-glutamic acid producing *Vibrio* bacterium can be constructed by modifying to enhance expression of a gene encoding an enzyme involved in L-glutamic acid biosynthesis. Examples of such enzymes include glutamate dehydrogenase (hereinafter, may be called "GDH") (gdh), glutamine synthetase (glnA), glutamate synthetase (gltAB), isocitrate dehydrogenase (icdA), aconitate hydratase (acnA, acnB), citrate synthase (gltA), phosphoenolpyruvate carboxylase (ppc), pyruvate dehydrogenase (aceEF, lpdA), pyruvate kinase (pykA, pykF), phosphoenolpyruvate synthase (ppsA), enolase (eno), phosphoglyceromutase (pgmA, pgmI), phosphoglycerate kinase (pgk), glyceraldehyde-3-phophate dehydrogenase (gapA), triose phosphate isomerase (tpiA), fructose bisphosphate aldolase (fbp), phosphofructokinase (pfkA, pfkB), glucose phosphate isomerase (pgi), and so forth. Among genes for these enzymes, one or more of CS, PEPC and GDH are examples (U.S. Pat. Nos. 6,197,559, 6,331,419, and EP0999282).

The bacterium may be modified to enhance activity of one or both of 6-phosphogluconate dehydratase and 2-keto-3-deoxy-6-phosphogluconate aldolase (EP1352966) or to amplify a yhfK gene encoding a protein that exports L-glutamic acid (WO2005/085419).

L-glutamic acid-producing *Vibrio* bacterium can have an activity of an enzyme that catalyzes synthesis of a compound other than L-glutamic acid by branching off from an L-glutamic acid biosynthesis pathway is decreased or eliminated. Examples of such enzymes include 2-oxoglutarate dehydrogenase, isocitrate lyase, phosphotransacetylase, acetate kinase, acetohydroxy acid synthase, acetolactate synthase, formate acetyltransferase, lactate dehydrogenase, and glutamate decarboxylase, and 1-pyrophosphate dehydrogenase. Decreasing or eliminating 2-oxoglutarate dehydrogenase activity is one example, and decreasing or eliminating 2-oxoglutarate dehydrogenase activity can be imparted according to EP0952221, EP0955368, and U.S. Pat. No. 5,378,616.

L-histidine-producing bacterium can have enhanced expression of a gene which encodes an L-histidine biosynthetic enzyme. Examples of such genes include the genes encoding ATP phosphoribosyltransferase (hisG), phosphoribosyl AMP cyclohydrolase (hisI), phosphoribosyl-ATP pyrophosphohydrolase (hisIE), phosphoribosylformimino-5-aminoimidazole carboxamide ribotide isomerase (hisA), amidotransferase (hisH), histidinol phosphate aminotransferase (hisC), histidinol phosphatase (hisB), and histidinol dehydrogenase (hisD).

L-histidine producing strains can also be obtained by imparting resistance to sulfaguanidine, D,L-1,2,4-triazole-3-alanine, and streptomycin (Russia 2,119,536).

L-cysteine producing strain can be constructed by imparting a modification to decrease cystathionine-β-lyase activity (JP2003-169668A) or to harbor serine acetyltransferase with decreased feedback inhibition with L-cysteine (JP11-155571A).

L-arginine-producing strain can be obtained by imparting resistance to α-methylmethionine, p-fluorophenylalanine, D-arginine, arginine hydroxamate, S-(2-aminoethyl)-cysteine, α-methylserine, β-2-thienylalanine or sulfaguanidine. L-arginine producing strain can also be bred by modifying so that N-acetylglutamate synthase has high activity and has a mutation that imparts resistance to feedback inhibition with L-arginine.

Examples of a *Vibrio* bacterium having L-arginine producing ability include strains in which expression of a gene encoding an L-arginine biosynthetic enzyme is enhanced. Examples of such genes include genes encoding N-acetylglutamate synthase (argA), N-acetylglutamyl phosphate reductase (argC), ornithine acetyl transferase (argJ), N-acetylglutamate kinase (argB), acetylornithine transaminase (argD), ornithine carbamoyl transferase (argF), argininosuccinic acid synthetase (argG), argininosuccinic acid lyase (argH), carbamoyl phosphate synthetase (carAB), and so forth.

Among these, a mutant gene encoding a mutant N-acetylglutamate synthase (argA) that is resistant to feedback inhibition with L-arginine due to the replacement of amino acids corresponding to positions 15 to 19 of a wild type enzyme (EP1170361A) is one example.

L-leucine-producing bacterium can be obtained by inactivating branched chain amino acid transaminase encoded by ilvE gene, and enhancing an activity of aromatic amino acid transaminase encoded by tyrB gene (JP2004-024259A) or by imparting resistance to 4-azaleucine or 5,5,5-trifluoroleucine. Furthermore, L-leucine-producing bacterium can be constructed by imparting a modification so that isopropylmalate synthase is desensitized to feedback inhibition with L-leucine (EP1067191) or imparting resistance to β-2-thienylalanine and β-hydroxyleucine (U.S. Pat. No. 5,763,231).

L-isoleucine-producing bacterium can be obtained by imparting resistance to 6-dimethylaminopurine (JP 5-304969 A), resistance to an isoleucine analogue such as thiaisoleucine and isoleucine hydroxamate (JP 5-130882 A), and resistance to DL-ethionine (JP 5-130882 A) or arginine hydroxamate (JP 5-130882 A). In addition, recombinant *Vibrio* bacterium can also be obtained by amplifying a gene encoding L-isoleucine biosynthetic enzyme such as threonine deaminase and acetohydroxate synthase with a plasmid (JP 2-458 A, JP 2-42988A, and JP 8-47397).

L-valine-producing bacterium can be constructed by modifying to introduce a mutation for lipo acid-auxotrophy (WO96/06926) or a mutation for ATPase deficiency or by introducing a DNA containing ilvGMEDA operon that expresses at least ilvG, ilvM, ilvE and ilvD. The ilvGMEDA operon is subject to regulation (attenuation) by L-valine, L-isoleucine, and/or L-leucine, so it is desirable to remove the region of the ilvGMEDA operon responsible for attenuation so that the produced L-valine cannot attenuate expression of the operon (U.S. Pat. No. 5,998,178). Furthermore, the ilvGMEDA operon preferably does not express threonine deaminase activity.

Expression of genes other than those encoding specific biosynthetic enzymes may also be enhanced in the L-amino acid producing bacterium, and examples of such genes include those encoding enzymes involved in sugar uptake, sugar metabolism (glycolytic pathway), and energy metabolism.

Genes involved in sugar metabolism include genes encoding enzymes in the glycolytic pathway or enzymes involved in sugar uptake. Examples thereof include the glucose-6-phosphate isomerase gene (pgi; WO 01/02542), phosphoenolpyruvate synthase gene (pps; EP 877090 A), phosphoglucomutase gene (pgm; WO 03/04598), fructose bisphosphate aldolase gene (fba; WO 03/04664), pyruvate kinase gene (pykF; WO 03/008609), transaldolase gene (talB; WO 03/008611), fumarase gene (fum; WO 01/02545), phosphoenolpyruvate synthase gene (pps; EP 877090 A), non-PTS sucrose uptake gene (csc; EP 149911 A), and sucrose-assimilating gene (scrAB operon; WO 90/04636).

Examples of genes encoding enzymes involved in energy metabolism include transhydrogenase gene (pntAB; U.S. Pat. No. 5,830,716) and cytochromoe bo type oxidase gene (cyoB; EP 1070376).

<3> L-Amino Acid Production Method

The L-amino acid production method includes steps such as cultivating a *Vibrio* bacterium bred as described above in a medium to produce and cause accumulation of an L-amino acid in the medium and collecting the L-amino acid from the medium or bacterial cells. The L-amino acid production method is a fermentation method to produce L-amino acid from a carbon source such as glucose and sucrose, and does not include the methods of producing L-amino acid from a precursor of L-amino acid using a *Vibrio* bacterium as a microbial catalyst as disclosed in JP 56-85291 A JP 62-275696 A, JP 60-62993 A, JP 63-216490 A, and JP 62-289194 A.

A conventional medium for fermentative production of an L-amino acid using a bacterium can be used. That is, a general medium containing a carbon source, nitrogen source, inorganic ion, and if necessary, other organic components can be used. Examples of the carbon source include sugars such as glucose, sucrose, lactose, galactose, fructose and a starch hydrolysate; alcohols such as glycerol and sorbitol; and organic acids such as fumaric acid, citric acid and succinic acid. Examples of the nitrogen source include inorganic ammonium salts such as ammonium sulfate, ammonium chloride and ammonium phosphate; an organic nitrogen such as a soybean hydrolysate; ammonia gas; and aqueous ammonia. As organic trace nutrients, auxotrophic substances such as vitamin B1 and L-homoserine, yeast extract, and the like are preferably contained in the medium in an appropriate amount. Besides such substances, if necessary, potassium phosphate, magnesium sulfate, iron ion, manganese ion, or the like may be added in small amounts. The medium for culturing the bacterium of the present invention preferably contains a certain concentration of salt. The salt may be a salt formed by the reaction of a target substance and counter ion or NaCl. The medium to be used in the present invention may be a natural medium or a synthetic medium as long as it contains a carbon source, nitrogen source, inorganic ion, and if necessary, other organic trace nutrients.

L-amino acids which improve the growth or productivity may be added. For example, L-threonine, L-homoserine, or L-isoleucine is preferably added in L-lysine fermentation, and L-isoleucine, L-lysine, L-glutamic acid, or L-homoserine is preferably added in L-threonine fermentation, and L-phenylalanine, or L-tyrosine is preferably added in L-tryptophan fermentation. These amino acids are usually added at a concentration of 0.01-10 g/L.

The culture is preferably performed under aerobic conditions for 1 to 7 days at a temperature of 24° C. to 37° C. and a pH of 5 to 9. The pH can be adjusted with an inorganic or organic acidic or alkaline substance, ammonia gas or the like. The L-amino acid can be collected from the fermentation liquid by a conventional method such as ion-exchange resin, precipitation, and other known methods. When the L-amino acid accumulates in the bacterial cells, the L-amino acid can be collected, for example, by disrupting the bacterial cells by ultrasonication or the like to release L-amino acid into the supernatant fraction, and then the bacterial cells are removed by centrifugation, followed by subjecting the resulting supernatant to an ion-exchange resin or the like.

It is typically more effective to cultivate the bacterium under high osmotic pressure conditions. Examples of high osmotic pressure conditions include conditions of not less than 925 mOsm, preferably not less than 1100 mOs, more preferably not less than 1500 mOsm.

In the case of L-lysine fermentation, conditions include conditions where not less than 61 g/L, in another example, not less than 79 g/L, and in another example, 115 g/L of L-lysine is accumulated.

In the case of performing direct fermentation using sugar as a raw material, it is more effective that the medium contains not less than 66 g/L, in another example, 94 g/L, in another example, 152 g/L of glucose, or not less than 66 g/L, in another example, 94 g/L, and in another example, 152 g/L of sucrose.

EXAMPLES

Example 1

Production of L-Lysine Using *Vibrio Natriegens* (*V. Natriegens*) Under High Osmotic Pressure (1) Preparation of L-lysine-Producing Strain By Imparting Resistance To L-Lysine Analogue, S-(2-Aminoethyl)-L-Cysteine (AEC) to *V. natriegens*

Preparation of AEC Resistant Strain from *V. Natriegens* Wild-Type Strain

To prepare a strain having resistance to an L-lysine analogue (AEC) from a *V. natriegens* wild-type IFO15636 strain (ATCC 14048, AJ13670), the IFO15636 strain was mutated with a mutagen, N-methyl-N'-nitro-N-nitrosoguanidine (NTG), as follows.

The *V. natriegens* wild-type strain was inoculated on LB-NaCl agar medium (containing 10 g/L Bacto-tryptone, 5 g/L Bacto-yeast extract, 30 g/L NaCl, 0.4 g/L $MgSO_4$, and 20 g/L agar, pH 7.0), and cultured at 37° C. for 6 hours. The bacterium which grew on the agar medium was inoculated to 4 ml of LB-NaCl medium (containing 10 g/L Bacto-tryptone, 5 g/L Bacto-yeast extract, 30 g/L NaCl, and 0.4 g/L $MgSO_4$, pH 7.0) in a 25-ml test tube, and cultured with shaking at 37° C. for 19 hours. The obtained culture (40 µl) was added to 50 ml of LB-NaCl medium in a 500-mL Sakaguchi flask, and the bacterium was cultured with shaking at 37° C. for 3 hours. The absorbance of the culture liquid at 660 nm after culture was found to be 0.34. The bacterial cells after culture were collected by centrifugation at 1,000×g for 10 minutes and suspended in 5 mL of ML medium (containing 2.0 g/L glucose, 1.5 g/L $Na_2HPO_4$, 1.5 g/L $KH_2PO_4$, 3.0 g/L $(NH_4)SO_4$, 15 g/L NaCl, 40 µM $MgSO_4$, 6 µM $FeCl_3$, 24.8 µM $CaCl_2$, 0.7 µM $ZnSO_4$, 0.7 µM $CuSO_4$, 0.8 µM $CoCl_2$, 1.7 µM $H_3BO_3$, 1.3 µM $Na_2MoO_4$, and 0.7 µM $MnCl_2$, pH 7.3). NTG was added to 1 mL of the suspension of the bacterial cells so that a final concentration became 5 µg/mL, and the whole was allowed to stand at 35° C. for 10 minutes. The NTG-treated bacterial cells were collected by centrifugation at 15,000×g for 30 seconds, and the cells were washed twice with 1 mL of ML medium and suspended in 1 mL of ML medium.

Strains having resistance to AEC were obtained from the mutated bacterial cells. Specifically, 50 µl (containing $10^8$ cells) of the suspension was inoculated to ML agar medium containing 0.1 g/L AEC (prepared by adding 20 g/L agar to ML medium), and the cells were cultured at 37° C., to thereby obtain strains capable of forming colonies. The number of colonies formed by the *V. natriegens* wild-type strain on ML agar medium containing 0.1 g/L AEC was one-tenth of the number of colonies formed by the NTG-treated strains. The number of strains which formed colonies 24 hours after culture was 55 (I), the number of strains which formed colonies 48 hours after culture was 59 (II), and the number of strains which formed colonies 72 hours after culture was 59 (III).

These strains were applied again on ML agar medium containing 0.1 g/L AEC and cultured at 37° C. for 18 hours to select strains capable of growing well. 28 strains were selected from the strains (I), 47 strains were selected from the strains (II), and 40 strains were selected from the strains (III). The resultant 115 strains in total were obtained as *V. natriegens* AEC-resistant strains.

Evaluation of L-Lysine Producing Ability of *V. natriegens* AEC-Resistant Strains The abilities to produce L-lysine of the 115 *V. natriegens* AEC-resistant strains were evaluated using 25-mL test tubes. In the following experiments, the concentrations of L-lysine and glucose were measured using a biotech analyzer AS-210 (Sakura Seiki Co., Ltd., Japan), and the absorbance (OD) at 660 nm was measured using DU-800 (Beckman Coulter, USA). In measurement of the concentration of L-lysine, the culture solution was not diluted. The concentration of glucose was measured for a solution obtained by diluting each culture to 20 folds. The OD was measured for a solution obtained by diluting each culture medium 51 fold.

First, the 115 *V. natriegens* AEC-resistant strains were inoculated to 4 mL of LB-NaCl medium in a 25-mL test tube and cultured with shaking at 37° C. for 18 hours. The resultant culture (100 μl) was inoculated to 4 mL of MS-NaCl medium (containing 40 g/L glucose, 2.0 g/L Yeast extract, 1.0 g/L $KH_2PO_4$, 24 g/L $(NH_4)SO_4$, 4 mM $MgSO_4$, 15 g/L NaCl, 36 μM $MnSO_4$, 36 μM $FeSO_4$, and 0.8 μM $CaCO_3$, pH 7.0) in a 25-mL test tube, and the cells were cultured with shaking at 37° C. 4 and 24 hours after the start of culture, the concentrations of L-lysine in the culture media were measured.

As a result, the AEC-resistant strains of sample Nos. 28-15, 28-28, 28-29, 28-36, and 29-29 were found to produce L-lysine in amounts of 0.7 mM or more 4 or 24 hours after start of culture (Table 1).

TABLE 1

| Sample No. | 4 hours after start of culture | 24 hours after start of culture |
|---|---|---|
| Wild-type | 0 | 0 |
| 28-15 | 0 | 0.9 |
| 28-28 | 0.9 | 0.8 |
| 28-29 | 0.8 | 0.9 |
| 28-36 | 0.7 | 0 |
| 29-29 | 0.2 | 0.8 |

The five strains were subjected to flask culture, and the abilities to produce L-lysine were evaluated. Specifically, the strains were cultured with shaking using 4 mL of LB-NaCl medium in a 25-mL test tube at 37° C. for 15 hours. 10 μl of the obtained cells were inoculated to 4 mL of LB-NaCl medium in a 25-mL test tube and culture was performed with shaking at 37° C. for 1.5 hours. Thereafter, each of the obtained cultures was inoculated to 20 mL of MS-NaCl medium in a 500-mL Sakaguchi flask so that the OD became 0.01, and culture was performed with shaking at 37° C. 4, 7, 9, and 24 hours after the start of culture, the concentrations of L-lysine and glucose and the OD in the culture media were measured.

Figure 2:
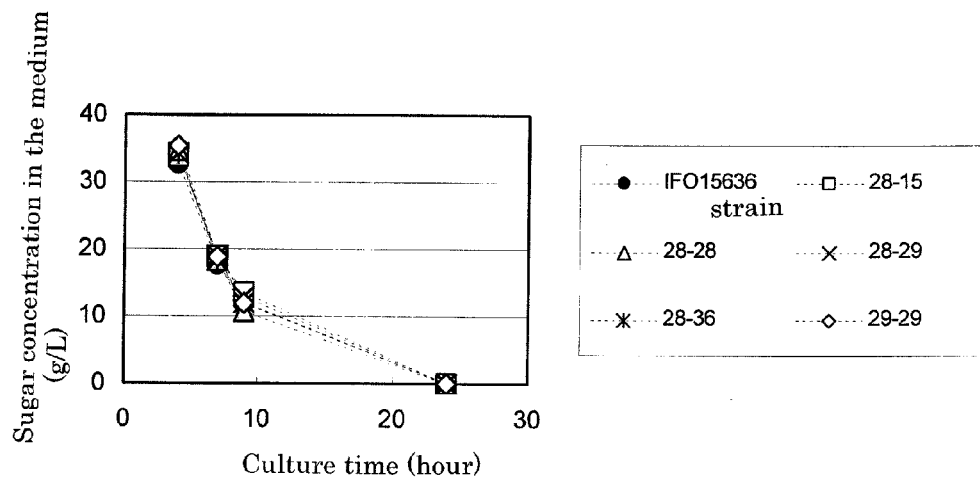
FIG. 2 is a graph showing changes in concentrations of glucose over time in culture media of the *V. natriegens* wild-type strain and AEC-resistant strains.
Figure 3:
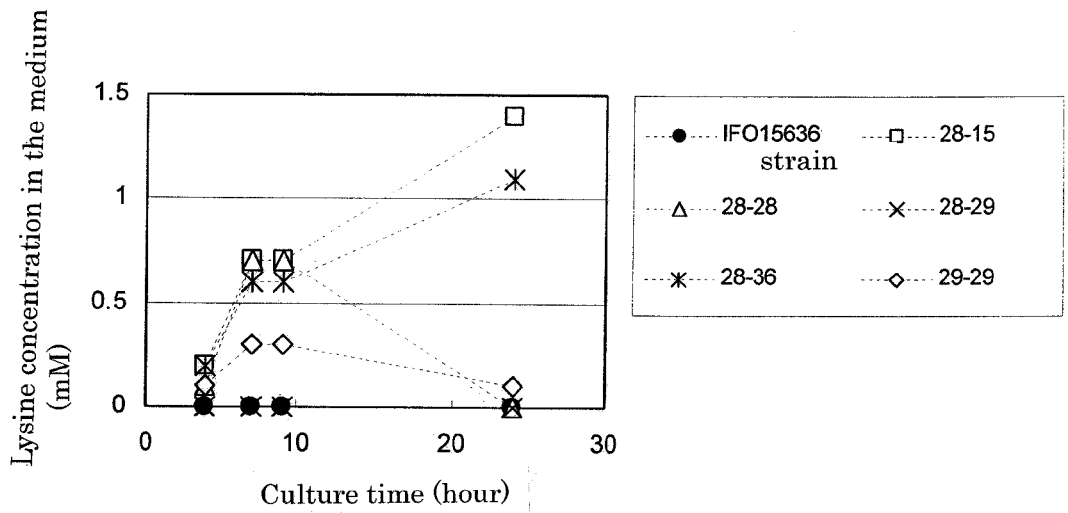
FIG. 3 is a graph showing changes in concentrations of lysine over time in culture media of the *V. natriegens* wild-type strain and AEC-resistant strains.

The results are shown in FIGS. 1, 2, and 3. The strain of the sample No. 28-15 (FERM BP-10946) was found to produce L-lysine at the highest level, and the maximum level of accumulated L-lysine was found to be 1.4 mM.

(2) Production of L-Lysine using *V. natriegens* Under High Osmotic Pressure

Production of L-lysine using *V. natriegens* under different osmotic pressures was compared with production of L-lysine using an *E. coli* L-lysine-producing stain. Specifically, the *V. natriegens* AEC-resistant Nos. 28-15 (FERM BP-10946), 28-28, and 28-29 strains, and a control strain, *E. coli* WC196 strain (refer to WO96/17930), were cultured in a medium containing 0.2 M to 1 M NaCl (osmotic pressure of the medium: 926 mOsm to 2,447 mOsm), and the amounts of L-lysine produced were measured. The medium, culture method, and analysis method are as follows.

MS medium:
Final concentration:

| | |
|---|---|
| Glucose | 40 g/L (sterilized separately) |
| $MgSO_4 \cdot 7H_2O$ | 1 g/L (sterilized separately) |
| $(NH_4)_2SO_4$ | 16 g/L |
| $KH_2PO_4$ | 1 g/L |
| Yeast Extract | 2 g/L |
| $FeSO_4$ | 0.01 g/L |
| $MnSO_4$ | 0.01 g/L |
| $CaCO_3$ | 30 g/L (sterilized separately) |

NaCl was added to have each final concentration of 0.2 M, 0.4 M, 0.6 M, 0.8 M, and 1 M.

Culture Method:

Pre-seed culture: *V. natriegens* in from storage was inoculated to LB+$MgSO_4$+NaCl agar medium (LB medium containing 0.4 g/l $MgSO_4$ and NaCl (final concentration: 3%)) and cultured at 34° C. *E. coli* was inoculated into LB agar medium and cultured at 37° C.

Seed test tube culture: the strains after the pre-seed culture were inoculated to LB+$MgSO_4$+NaCl liquid medium (*V. natriegens*) or LB liquid medium (*E. coli*) and cultured at 37° C. for 16 hours.

Main culture: 1 ml of the seed culture was inoculated to 20 ml of MS liquid medium and cultured in a 500-ml volume Sakaguchi flask at 37° C.

Analysis Method:

The concentrations of glucose and L-lysine were measured using a biotech analyzer AS-210 (Sakura Seiki Co., Ltd.) for a solution prepared by diluting a supernatant obtained by centrifuging each culture at 15,000 rpm for 5 minutes with water to an appropriate concentration. The osmotic pressure was measured using Advanced Osmometer Model 3900 manufactured by Advanced Instruments, Inc., USA.

Figure 4:
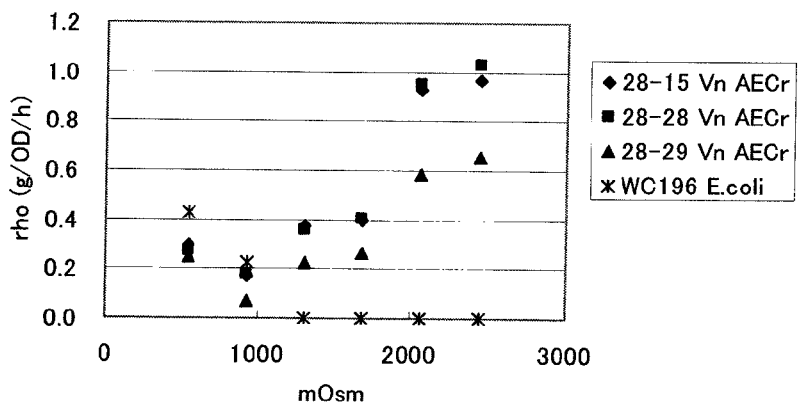
FIG. 4 is a graph showing maximum specific L-lysine production rates of an *E. coli* wild-type strain and *V. natriegens* AEC-resistant strains at different osmotic pressures.

FIG. 4 shows the maximum specific L-lysine production rates under different osmotic pressures. The results reveal that *E. coli* WC196 strain cannot produce L-lysine under high osmotic pressures, while the *V. natriegens* AEC-resistant strains, Nos. 28-15, 28-28, and 28-29, can produce L-lysine in large amounts even under high osmotic pressures.

Example 2

Growth of *V. Natriegens* under High Osmotic Pressure with L-Lysine

Growth of *V. natriegens* and *E. coli* at a high concentration of L-lysine was compared and observed.

The *V. natriegens* wild-type strain (IFO15636 strain) was inoculated to LB-NaCl agar medium (containing 10 g/L Bacto-tryptone, 5 g/L Bacto-yeast extract, 30 g/L NaCl, 0.4 g/L $MgSO_4$, and 20 g/L agar, pH 7.0), and cultured at 37° C.

for 15 hours. The strain which grew on the agar medium was inoculated to M9-NaCl medium (15 g/L NaCl, 6.0 g/L Na$_2$HPO$_4$, 3.0 g/L KH$_2$PO$_4$, 1.0 g/L NH$_4$Cl, 1.0 mM CaCl$_2$, 0.1 mM MgSO$_4$, 4.8 µM CaCl$_2$, 0.7 µM ZnSO$_4$, 0.7 µM CuSO$_4$, 0.8 µM CoCl$_2$, 1.7 µM H$_3$BO$_3$, 1.3 µM Na$_2$MoO$_4$, and 0.7 µM MnCl$_2$, pH 7.0) containing 0.2% glucose, and cultured at 30° C. for 24 hours. The turbidity after culture was measured using a spectrophotometer DU-800 (Beckman Coulter, Inc., USA) at a wavelength of 660 nm and was found to be 0.67. The obtained culture (60 µl) was inoculated to 4 mL of each of 6 kinds of M9 media (containing 0.05, 0.27, 0.55, 0.82, 1.1, and 1.4 M L-lysine) each containing 0.04% glucose, and the cells were cultured using a small shaking culture apparatus (TN-1506, Advantec Toyo Kaisha, Ltd., Japan) at 30° C., and the absorbance at 660 nm was observed every 15 minutes.

Further, the *E. coli* wild-type strain (ATCC No. 47076 strain) was inoculated into LB agar medium (containing 10 g/L Bacto-tryptone, 5 g/L Bacto-yeast extract, 5 g/L NaCl, and 20 g/L agar, pH 7.0), and cultured at 37° C. for 15 hours. The strain grown on the agar medium was inoculated to M9 medium (6.0 g/L Na$_2$HPO$_4$, 3.0 g/L KH$_2$PO$_4$, 1.0 g/L NH$_4$Cl, 1.0 mM CaCl$_2$, 0.1 mM MgSO$_4$, 4.8 µM CaCl$_2$, 0.7 µM ZnSO$_4$, 0.7 µM CuSO$_4$, 0.8 µM CoCl$_2$, 1.7 µM H$_3$BO$_3$, 1.3 µM Na$_2$MoO$_4$, and 0.7 µM MnCl$_2$, pH 7.0) containing 0.2% glucose, and cultured at 30° C. for 24 hours. The turbidity after culture was found to be 0.67. The obtained culture (60 µl) was inoculated into 4 mL of each of 6 kinds of M9 media (containing 0.05, 0.27, 0.55, 0.82, 1.1, and 1.4 M L-lysine) each containing 0.04% glucose, and the cells were cultured using a small shaking culture apparatus TN-1506 at 30° C., and the absorbance at 660 nm, OD660, was observed every 15 minutes.

The maximum specific growth rates were calculated based on the growth curves of *V. natriegens* and *E. coli* and compared. The maximum specific growth rates were determined as follows. The specific growth rates were calculated every 15 minutes according to the following formula.

Specific growth rate (h$^{-1}$)=4×(ln(OD660 at t$_1$)−ln(OD660 at t$_0$))

[the difference between t$_1$ and t$_0$ is 15 minutes].

Then, the maximum value of the specific growth rates was defined as the maximum specific growth rate for each condition.

The osmotic pressure of M9 medium containing each concentration of L-lysine was determined by measurement for each medium before inoculation of the strain using advanced CRYOMATIC™ Osmometer (Advanced Instruments, Inc., USA).

Figure 5:
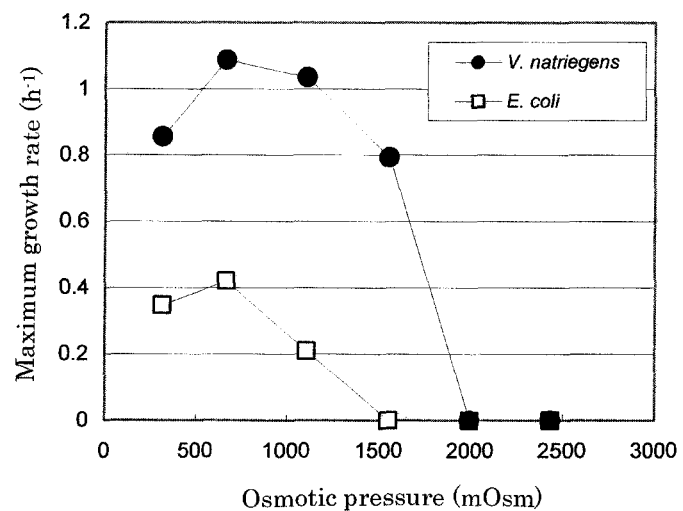
FIG. 5 is a graph showing growth rates of *E. coli* and *V. natriegens* under high osmotic pressure with L-lysine.

From the results of observation of the culture, *V. natriegens* was found to grow under an osmotic pressure of 1,550 mOsm (concentration of L-lysine: 0.8 M), while *E. coli* was found not to grow (FIG. 5).

Meanwhile, at all the L-lysine concentrations where growth was observed, *V. natriegens* was found to grow at higher rate compared with *E. coli*. The lowest maximum specific growth rate (observed at an osmotic pressure of 1,550 mOsm) of *V. natriegens* which has been observed was found to be 0.79 h$^{-1}$, which is 1.7 times as much as the highest maximum specific growth rate (observed at an osmotic pressure of 670 mOsm) of *E. coli*.

Example 3

Growth of *V. Natriegens* under High Osmotic Pressure with Glucose

The *V. natriegens* wild-type strain (IFO15636 strain) was inoculated on LB-NaCl agar medium and cultured at 37° C. for 6 hours. The cells which grew on the agar medium were inoculated on 4 mL of LB-NaCl medium and cultured at 37° C. for 14 hours. The obtained culture (8 µL) was inoculated to 4 mL of LB-NaCl medium and culture was performed at 37° C. for 3.5 hours. The absorbance at 660 nm (OD660) after culture was found to be 1.7. The obtained culture of the *V. natriegens* wild-type strain (471 µl) was added to MS medium (2.0 g/L Yeast extract, 1.0 g/L KH$_2$PO$_4$, 24 g/L (NH$_4$)SO$_4$, 4 mM MgSO$_4$, 36 µM MnSO$_4$, 36 µM FeSO$_4$, and 0.8 µM CaCO$_3$. pH 7.0) containing 0.2 to 0.8 M glucose, and the cells were cultured at 37° C. The OD660 and concentration of glucose in the culture medium were observed with time.

Meanwhile, an *E. coli* wild-type strain (W3110 strain) was inoculated on LB agar medium and cultured at 37° C. for 6 hours. The cells grown on the agar medium were inoculated to 4 mL of LB medium and culture was performed at 37° C. for 14 hours. The obtained culture (8 µL) was inoculated to 4 mL of LB medium and culture was performed at 37° C. for 3.5 hours. The OD660 after culture was 0.9. The obtained culture of the *E. coli* wild-type strain (889 µl) was inoculated into MS medium containing 0.2 to 0.8 M glucose, and the cells were cultured at 37° C. The OD660 and concentration of glucose in the culture medium were observed with time.

The OD660 was measured using a spectrophotometer (U-2001, Hitachi, Ltd., Japan). The concentration of glucose was measured using a biotech analyzer AS-210 (Sakura Seiki Co., Ltd., Japan). The osmotic pressure of MS medium at each glucose concentration was determined by measurement for each medium before inoculation of the strain using advanced CRYOMATIC™ Osmometer (ADVANCED INSTRUMENTS, Inc., USA).

From changes in the OD660 and concentrations of glucose, the specific glucose consumption rates under different osmotic pressures 4.5 hours after the start of culture were calculated and compared.

Figure 6:
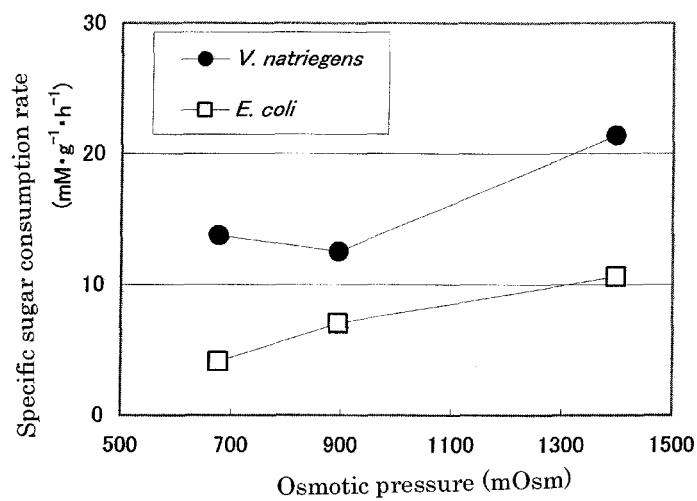
FIG. 6 is a graph showing glucose consumption rates of *E. coli* and *V. natriegens* under high osmotic pressure with glucose.

As a result, the specific glucose consumption rates of *V. natriegens* were found to be higher than those of *E. coli* (FIG. 6).

Example 4

Production of L-Lysine by Enhancement of L-Lysine Biosynthesis of *V. Natriegens*

A plasmid carrying L-lysine biosynthetic genes (lysC, dapA, dapB, and ddh), pCABD2, was introduced into the *V. natriegens* wild-type strain AJ13670 (IFO15636), and AEC-resistant strains Nos. 28-15 (FERM BP-10946), 28-28, and 28-29 strains, respectively, and the obtained strains were cultured to produce L-lysine. As controls, only a vector pRS was introduced into the respective strains, and the strains were cultured in the same way as described above. Introduction of each plasmid DNA into *V. natriegens* was performed by electroporation as follows. The bacterial cells were cultured in LB medium containing 0.4 g/l MgSO$_4$ and NaCl (final concentration: 3%) until the late logarithmic growth phase (OD=0.6 to 0.8) and washed three times with 2 mM HEPES (pH 6.8) containing 100 mM sucrose and 5 mM CaCl$_2$. Thereafter, the cells were suspended in 10% glycerol, and the plasmid DNA was added thereto. Then, the cells were cultured with shaking at 34° C. for 2 to 3 hours in LB medium containing 0.4 g/l MgSO$_4$, NaCl (final concentration: 3%), and 0.4% glucose, and clones into which the plasmid was introduced were selected on LB agar medium containing 500 mg/l streptomycin, 0.4 g/l MgSO$_4$, and NaCl (final concentration: 3%). The obtained strains were cultured in the same way as in Example 1. Culture including pre-seed culture, seed test tube culture, and main culture was performed at 34° C., and 500 mg/l streptomycin was added to the medium. In the main culture, MS medium containing NaCl at a final concentration of 0.5% was used. Table 2 shows the OD measured 9.3 hours after the start of culture, concentrations of L-lysine accumulated in the medium, and yield per consumed glucose. From the results, the abilities to produce L-lysine of *V. natriegens* Nos. 28-15, 28-28, and 28-29 strains were found to be further improved by introducing the L-lysine biosynthesis genes.

TABLE 2

| strain | OD | Lys(g/l) | Yield (%) |
|---|---|---|---|
| AJ13670/pCABD2 | 17.8 | 0.310 | 1.2 |
| 28-15/pCABD2 | 16.5 | 0.342 | 1.4 |
| 28-28/pCABD2 | 16.9 | 0.535 | 2.2 |
| 28-29/pCABD2 | 15.8 | 0.471 | 2.0 |
| AJ13670/pRS | 19.8 | 0.002 | 0.0 |
| 28-15/pRS | 18.1 | 0.125 | 0.5 |
| 28-28/pRS | 17.4 | 0.128 | 0.5 |
| 28-29/pRS | 19.6 | 0.096 | 0.3 |

Example 5

Production of L-Lysine by Amplification of AK Gene

Preparation of AK (Aspartokinase) Gene of *V. Natriegens*

To determine the nucleotide sequence of the AKO gene of *V. natriegens*, oligonucleotides of SEQ ID NOs: 1 to 4 were synthesized based on nucleotide sequences conserved in AKO genes (NCBI-GeneID: 2615216, 1190071, and 1178506) of the above-mentioned *Vibrio* bacteria (*Vibrio cholerae*, *Vibrio parahaemolyticus*, and *Vibrio vulnificus*) whose genome had been identified. Meanwhile, to determine the sequences of thrA, metL, lysC (AKIII gene), and putative AK gene of *V. natriegens*, oligonucleotides were synthesized based on nucleotide sequences of thrA (NCBI-GeneID: 2613033, 1187962, and 1177497), metL (NCBI-GeneID: 2615512, 1190314, and 1178287), lysC (AKIII gene) (NCBI-GeneID: 2614988, 1190261, and 1178339), and putative AK gene (NCBI-GeneID: 2612362 and 1189226) conserved among the species of the above-mentioned *Vibrio* bacteria. Specifically: to identify the nucleotide sequence of thrA, oligonucleotides of SEQ ID NOS: 5 to 11 were synthesized; to identify the nucleotide sequence of metL, oligonucleotides of SEQ ID NOS: 12 to 16 were synthesized; to identify the nucleotide sequence of lysC, oligonucleotides of SEQ ID NOS: 17 and 18 were synthesized; and to identify the nucleotide sequence of putative AK gene, oligonucleotides of SEQ ID NOS: 19 and 20 were synthesized. In SEQ ID NOS: 1 to 20: "r" means either g or a; "y" means either t or c; "m" means either a or c; "k" means either g or t; "s" means either g or c; and "w" means either a or t. For example, "T(C/T)G" means a mixture of the oligonucleotides TCG and TTG.

Partial fragments of the genes were obtained by performing PCR using the oligonucleotides prepared based on conserved sequences as primers and a genomic DNA of *V. natriegens* IFO15636 strain (wild-type strain) as a template. Specifically, PCR was performed using primers as shown in Table 3 in combination. The genomic DNA was prepared using DNeasy Tissue Kit (QIAGEN, Germany). PCR was performed as follows: a reaction at 98° C. for 1 minute was performed; then a cycle including 98° C. for 10 seconds, 55° C. for 30 seconds, and 72° C. for 90 seconds was repeated 30 times; and then a reaction at 72° C. for 10 minutes was performed. Unreacted primers and dNTP's in the resultant PCR products were removed using MicroSpin S-400 HR (GE healthcare, USA), and the products were used in the following experiment.

Next, the nucleotide sequences of partial fragments of the AK gene homologues were determined using the resultant partial fragments of the genes as templates and the oligonucleotides used in amplification of the genes as primers and using CEQ dye termination cycle sequencing with Quick start kit (Beckman Coulter, USA). Oligonucleotides complementary to the identified nucleotide sequences of the partial fragments of the AK gene homologues were sequentially synthesized based on the sequences, and the nucleotide sequences of the partial fragments of the genes were identified.

Subsequently, the upstream and downstream regions of the thus-obtained partial gene fragments were obtained using Takara LA PCR in vitro cloning kit (Takara Bio Inc., Japan) to determine the nucleotide sequences.

As a result, the nucleotide sequences on the upstream and downstream regions of the partial fragments of AKO gene (0.6 kbp and 0.2 kbp), thrA (0.8 kbp and 0.4 kbp), metL (0.4 kbp and 0.5 kbp), lysC (0.4 kbp and 1.0 kbp), and putative AK gene (0.4 kbp and 0.8 kbp) of *V. natriegens* were identified, and thereby the nucleotide sequences of AKO gene (1,779 bp, SEQ ID NO: 21), thrA (3,547 bp, SEQ ID NO: 23), metL (3,214 bp, SEQ ID NO: 25), lysC (2,648 bp, SEQ ID NO: 27), and putative AK gene (2,331 bp, SEQ ID NO: 29) of *V. natriegens* were identified.

TABLE 3

Combination of primers and the length of each of the obtained partial gene fragments

| target gene | Combination of primers and the length of amplified DNA |
|---|---|
| AKO gene | (SEQ ID NO: 1, SEQ ID NO: 3; 0.5 kbp) |
|  | (SEQ ID NO: 1, SEQ ID NO: 4; 1.1 kbp) |
|  | (SEQ ID NO: 2, SEQ ID NO: 4; 0.6 kbp) |
| thrA | (SEQ ID NO: 5, SEQ ID NO: 9; 0.8 kbp) |
|  | (SEQ ID NO: 6, SEQ ID NO: 10; 1.4 kbp) |
|  | (SEQ ID NO: 7, SEQ ID NO: 10; 1.0 kbp) |
|  | (SEQ ID NO: 8, SEQ ID NO: 11; 1.1 kbp) |
| metL | (SEQ ID NO: 12, SEQ ID NO: 16; 2.3 kbp) |
|  | (SEQ ID NO: 13, SEQ ID NO: 15; 0.9 kbp) |
|  | (SEQ ID NO: 13, SEQ ID NO: 16; 1.7 kbp) |
|  | (SEQ ID NO: 14, SEQ ID NO: 16; 0.8 kbp) |
| lysC (AK III gene) | (SEQ ID NO: 17, SEQ ID NO: 18; 1.4 kbp) |
| ptative AK gene | (SEQ ID NO: 19, SEQ ID NO: 20; 1.0 kbp) |

Next, an open reading frame (ORF) analysis was performed for the above-mentioned 5 kinds of AK genes by GENETYX network version 7.0.6 (GENETYX CORPORATION, Japan). As a result, the start codon of AKO gene was found to be GTG corresponding to nucleotide numbers 526 to 528, GTG corresponding to nucleotide numbers 544 to 546, or GTG corresponding to nucleotide numbers 568 to 570 in SEQ ID NO: 21, while the stop codon was found to be TGA corresponding to nucleotide numbers 1,711 to 1,713. The start codon of thrA was found to be ATG corresponding to nucleotide numbers 486 to 488, GTG corresponding to nucleotide numbers 591 to 593, or GTG corresponding to nucleotide numbers 633 to 635 in SEQ ID NO: 23, while the stop codon was found to be TAA corresponding to nucleotide numbers 2,943 to 2,945. The start codon of metL was found to be ATG corresponding to nucleotide numbers 376 to 378, GTG corresponding to nucleotide numbers 487 to 489, or GTG corresponding to nucleotide numbers 490 to 492 in SEQ ID NO: 25, while the stop codon was found to be TAA corresponding to nucleotide numbers 2,782 to 2,784. The start codon of lysC was found to be GTG corresponding to nucleotide numbers 1,060 to 1,062 or ATG corresponding to nucleotide numbers 1,117 to 1,119 in SEQ ID NO: 27, while the stop codon was found to be TAA corresponding to nucleotide numbers 2,410 to 2,412. The start codon of putative AK gene was found to be ATG corresponding to nucleotide numbers 344 to 346, ATG corresponding to nucleotide numbers 380 to 382, or ATG corresponding to nucleotide numbers 470 to 472 in SEQ ID NO: 29, while the stop codon was found to be TAA corresponding to nucleotide numbers 1,766 to 1,768.

Cloning of *V. natriegens* Aspartokinase Gene

To clone AKO gene, PCR was performed using a genomic DNA of the *V. natriegens* wild-type strain (IFO15636 strain) prepared using DNeasy Tissue kit (QIAGEN, Germany) as a template and oligonucleotides of SEQ ID NOS: 31 and 32 as primers. PCR was performed as follows: a reaction at 98° C. for 1 minute was performed; a cycle including 98° C. for 10 seconds, 55° C. for 30 seconds, and 72° C. for 150 seconds was repeated 30 times; and then a reaction at 72° C. for 5 minutes was performed. Unreacted primers and dNTP's in the resultant PCR products were removed using MicroSpin S-400 HR (GE healthcare, USA), to thereby obtain a DNA fragment containing full-length AKO gene.

The resultant DNA fragment containing AKO gene was treated with SmaI and EcoRI (Takara Bio Inc., Japan) at 37° C. for 60 minutes. Subsequently, the AKO gene treated with the restriction enzymes was ligated to a vector pSTV28, which had been treated with SmaI and EcoRI in the same way, to thereby obtain pSTV28#AKO.

To clone thrA, metL, lysC, and putative AK gene of *V. natriegens* in the same way as described above, PCR was performed using, as primers, oligonucleotides of SEQ ID NOS: 33 and 34 for amplification of thrA, oligonucleotides of SEQ ID NOS: 35 and 36 for amplification of metL, oligonucleotides of SEQ ID NOS: 37 and 38 for amplification of lysC, or oligonucleotides of SEQ ID NOS: 39 and 40 for amplification of putative AK gene under the same conditions as those in the case of AKO gene, to thereby obtain DNA fragments containing full-length thrA, metL, lysC, and putative AK gene, respectively.

Among the resultant DNA fragments, the fragment containing metL was treated with restriction enzymes SmaI (Takara Bio Inc., Japan) and SacI (Takara Bio Inc., Japan) at 37° C. for 60 minutes. The fragment containing metL obtained by treating with the restriction enzymes was ligated to the vector pSTV28, which had been treated with SmaI and SacI in the same way, to thereby obtain pSTV28#AKII.

Meanwhile, among the resultant DNA fragments, the fragments each containing thrA, lysC, and putative AK gene were treated with SmaI and EcoRI (Takara Bio Inc., Japan) at 37° C. for 60 minutes. The fragments each containing thrA, lysC, and putative AK gene obtained by the restriction enzyme treatment were ligated to the vector pSTV28, which had been treated with SmaI and EcoRI in the same way, to thereby obtain pSTV28#AKI, pSTV28#AKIII, and pSTV28#putative-AK, respectively.

By appropriately enhancing the AK activity with the resultant AK genes or their gene sequences, a *Vibrio* bacterium having an improved L-lysine-producing ability can be constructed and used for production of L-lysine.

As vector plasmids, any plasmids may be used as long as they have ori derived from pUC plasmids, pACYC184 plasmids, and IncQ plasmid. The marker gene which is used for selection may be a kanamycin-resistant gene derived from Tn903, a chloramphenicol-resistant gene derived from Tn9, a streptomycin-resistant gene, or a tetracycline-resistant gene.

Explanation about the Sequence Listing:

SEQ ID NO: 1: Nucleotide sequence of the primer for sequencing AKO gene
SEQ ID NO: 2: Nucleotide sequence of the primer for sequencing AKO gene
SEQ ID NO: 3: Nucleotide sequence of the primer for sequencing AKO gene
SEQ ID NO: 4: Nucleotide sequence of the primer for sequencing AKO gene
SEQ ID NO: 5: Nucleotide sequence of the primer for sequencing thrA gene
SEQ ID NO: 6: Nucleotide sequence of the primer for sequencing thrA gene
SEQ ID NO: 7: Nucleotide sequence of the primer for sequencing thrA gene
SEQ ID NO: 8: Nucleotide sequence of the primer for sequencing thrA gene
SEQ ID NO: 9: Nucleotide sequence of the primer for sequencing thrA gene
SEQ ID NO: 10: Nucleotide sequence of the primer for sequencing thrA gene
SEQ ID NO: 11: Nucleotide sequence of the primer for sequencing thrA gene
SEQ ID NO: 12: Nucleotide sequence of the primer for sequencing metL gene
SEQ ID NO: 13: Nucleotide sequence of the primer for sequencing metL gene
SEQ ID NO: 14: Nucleotide sequence of the primer for sequencing metL gene
SEQ ID NO: 15: Nucleotide sequence of the primer for sequencing metL gene
SEQ ID NO: 16: Nucleotide sequence of the primer for sequencing metL gene
SEQ ID NO: 17: Nucleotide sequence of the primer for sequencing lysC gene
SEQ ID NO: 18: Nucleotide sequence of the primer for sequencing lysC gene
SEQ ID NO: 19: Nucleotide sequence of the primer for sequencing putative-AK gene
SEQ ID NO: 20: Nucleotide sequence of the primer for sequencing putative-AK gene
SEQ ID NO: 21: Nucleotide sequence of the AKO gene from *V. natriegens*
SEQ ID NO: 22: Amino acid sequence encoded by the AKO gene from *V. natriegens*
SEQ ID NO: 23: Nucleotide sequence of the thrA gene from *V. natriegens*
SEQ ID NO: 24: Amino acid sequence encoded by the thrA gene from *V. natriegens*
SEQ ID NO: 25: Nucleotide sequence of the metL gene from *V. natriegens*
SEQ ID NO: 26: Amino acid sequence encoded by the metL gene from *V. natriegens*
SEQ ID NO: 27: Nucleotide sequence of the lysC gene from *V. natriegens*
SEQ ID NO: 28: Amino acid sequence encoded by the lysC gene from *V. natriegens*
SEQ ID NO: 29: Nucleotide sequence of the putative-AK gene from *V. natriegens*
SEQ ID NO: 30: Amino acid sequence encoded by the putative-AK gene from *V. natriegens* SEQ ID NO: 31: Nucleotide sequence of the primer for amplifying the AKO gene
SEQ ID NO: 32: Nucleotide sequence of the primer for amplifying the AKO gene
SEQ ID NO: 33: Nucleotide sequence of the primer for amplifying the thrA gene SEQ ID NO: 34: Nucleotide sequence of the primer for amplifying the thrA gene
SEQ ID NO: 35: Nucleotide sequence of the primer for amplifying the metL gene
SEQ ID NO: 36: Nucleotide sequence of the primer for amplifying the metL gene
SEQ ID NO: 37: Nucleotide sequence of the primer for amplifying the lysC gene
SEQ ID NO: 38: Nucleotide sequence of the primer for amplifying the lysC gene
SEQ ID NO: 39: Nucleotide sequence of the primer for amplifying the putative-AK gene
SEQ ID NO: 40: Nucleotide sequence of the primer for amplifying the putative-AK gene

INDUSTRIAL APPLICABILITY

According to the present invention, an L-amino acid is efficiently produced. Specifically, it was found that L-amino acid-producing ability of the *Vibrio* bacterium does not decrease and its growth is not inhibited under high osmotic pressure conditions, so by using the bacterium, L-amino acids can be very efficiently produced even under high osmotic pressure conditions.

While the invention has been described in detail with reference to exemplary embodiments thereof, it will be apparent to one skilled in the art that various changes can be made, and equivalents employed, without departing from the scope of the invention. Each of the aforementioned documents is incorporated by reference herein in its entirety.

What is claimed is:

1. A method for producing L lysine by fermentation, comprising:

culturing a *Vibrio* bacterium having L-lysine-producing ability in a medium under high osmotic pressure not less than 925 mOsm to produce and accumulate the L-lysine in the medium; and collecting the L-lysine from the medium, and wherein the *Vibrio* bacterium is selected from the group consisting of *Vibrio abalonicus, Vibrio adaptatus, Vibrio aerogenes, Vibrio aestuarianus, Vibrio alginolyticus, Vibrio algosus, Vibrio anguillarum, Vibrio calviensis, Vibrio campbellii, Vibrio carchariae, Vibrio coralliilyticus, Vibrio costicola, Vibrio cyclitrophicus, Vibrio cyclosites, Vibrio diazotrophicus, Vibrio fischeri, Vibrio gazogenes, Vibrio halioticoli, Vibrio harveyi, Vibrio hispanica, Vibrio ichthyoenteri, Vibrio iliopisacarius, Vibrio lentus, Vibrio liquefaciens, Vibrio logei, Vibrio marinagilis, Vibrio marinofulvus, Vibrio marinovulgaris, Vibrio mediterranei, Vibrio metschnikovii, Vibrio mytili, Vibrio natriegenes, Vibrio navarrensis, Vibrio nereis, Vibrio nigripulchritudo, Vibrio ordalii, Vibrio oreintalis, Vibrio pectenicida, Vibrio pelagius, Vibrio penaeicida, Vibrio ponticus, Vibrio proteolyticus, Vibrio psychroerythrus, Vibrio salmonicida, Vibrio shiloii, Vibrio splendidus, Vibrio tyrosinaticus, Vibrio viscosus,* and *Vibrio wondanis.*

2. The method of claim 1, wherein the L-lysine producing ability is imparted to the bacterium by imparting resistance to an L-lysine analogue.

3. The method of claim 1, wherein the bacterium has an enhanced activity of an L-lysine biosynthesis enzyme.

4. The method of claim 2, wherein the L-lysine analogue is selected from the group consisting of S-(2-aminoethyl)-L-cystein (AEC), oxalysine, lysine hydroxamate, γ-methyl lysine, α-chlorocaprolactam, DL-α-amino-ε-caprolactam, α-amino-lauryllactam, asparaginic acid analogue, a sulfa drug, quinoid, N-lauroyl leucine, and combinations thereof.

5. The method of claim 3, wherein the L-lysine biosynthesis enzyme is selected from the group consisting of dihydropicolate synthase, aspartokinase, aspartate-semialdehyde dehydrogenase, dihydropicolinate reductase, diaminopimelate decarboxylase, and combinations thereof.

6. The method of claim 5, wherein the dihydropicolate synthase and the aspartokinase are modified to be resistant to feedback inhibition by L-lysine.

7. The method of claim 4, wherein the bacterium is further modified so that the L-lysine export activity is enhanced.

* * * * *